United States Patent
Kamei et al.

(10) Patent No.: US 7,202,041 B2
(45) Date of Patent: Apr. 10, 2007

(54) IMMUNOREACTION MEASUREMENT METHOD

(75) Inventors: Akihito Kamei, Yawata (JP); Tatsurou Kawamura, Kyotanabe (JP); Keiko Yugawa, Nara (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 31 days.

(21) Appl. No.: 10/516,067

(22) PCT Filed: Dec. 9, 2003

(86) PCT No.: PCT/JP03/15754

§ 371 (c)(1),
(2), (4) Date: Nov. 29, 2004

(87) PCT Pub. No.: WO2004/053489

PCT Pub. Date: Jun. 24, 2004

(65) Prior Publication Data

US 2005/0176063 A1    Aug. 11, 2005

(30) Foreign Application Priority Data

Dec. 10, 2002  (JP) .............................. 2002-357459
Dec. 16, 2002  (JP) .............................. 2002-364195

(51) Int. Cl.
  *G01N 33/53* (2006.01)
  *G01N 33/536* (2006.01)
  *G01N 21/00* (2006.01)
  *C07K 16/00* (2006.01)

(52) U.S. Cl. .................. 435/7.1; 435/961; 436/164; 436/501; 436/536; 436/805; 530/362; 530/388.9

(58) Field of Classification Search ............... 435/7.1, 435/7.92–7.94, 967, 961; 436/501, 518, 436/524, 164, 805, 825, 536; 530/362, 388.9
See application file for complete search history.

(56) References Cited

U.S. PATENT DOCUMENTS 3,962,413 A * 6/1976 George et al. ............ 435/7.32
4,628,035 A * 12/1986 Tokinaga et al. ......... 435/7.94
4,672,045 A * 6/1987 Tsutsui et al. ............. 436/518
4,931,385 A * 6/1990 Block et al. ............... 435/7.94
5,658,725 A   8/1997 Schlieper et al.
2003/0166302 A1 * 9/2003 Shigenobu et al. ........ 436/518

FOREIGN PATENT DOCUMENTS

| JP | 2-61561   | 3/1990  |
|----|-----------|---------|
| JP | 6-82450   | 3/1994  |
| JP | 9-89894   | 4/1997  |
| JP | 10-332694 | 12/1998 |
| JP | 11-344494 | 12/1999 |

* cited by examiner

Primary Examiner—Long V. Le
Assistant Examiner—Shafiqul Haq
(74) Attorney, Agent, or Firm—McDermott Will & Emery LLP

(57) ABSTRACT

The present invention relates to an immunoreaction measuring method for measuring an antigen or antibody contained as a subject substance in a sample, wherein the sample was mixed with at least one compound selected from the group consisting of dicarboxylic acids having a hydroxyl group, dicarboxylic acids having a double bond, straight-chain dicarboxylic acids expressed by the chemical formula (1): $HOOC(CH_2)_nCOOH$ (n is an integer), and the salts of these dicarboxylic acids, and an antibody or antigen as a specifically binding substance capable of specifically binding to the subject substance, to obtain an acidic reaction solution, and then an antigen-antibody complex, generated by an antigen-antibody reaction of the subject substance with the specifically binding substance in the reaction solution was detected. This makes it possible to improve a measurement value and to relax a limitation of a measurement range due to a zone phenomenon that occurs in an antigen-excess region.

12 Claims, 18 Drawing Sheets

- ● 0.05 M L(−)-malic acid, 4 wt% PEG 6000, pH 4.5
- ○ 0.05 M L(+)-tartaric acid, 4 wt% PEG 6000, pH 4.5
- ▲ 0.05 M itaconic acid, 4 wt% PEG 6000, pH 4.5
- × 0.05 M MOPS, 4 wt% PEG 6000, pH 7.4

- ● 0.01 M L(-)-malic acid, 4 wt% PEG 6000, pH 5.0
- ○ 0.02 M L(-)-malic acid, 4 wt% PEG 6000, pH 5.0
- ▲ 0.05 M L(-)-malic acid, 4 wt% PEG 6000, pH 5.0
- △ 0.1 M L(-)-malic acid, 4 wt% PEG 6000, pH 5.0
- ■ 0.2 M L(-)-malic acid, 4 wt% PEG 6000, pH 5.0
- × 0.05 M MOPS, 4 wt% PEG 6000, pH 7.4

- ● 0.02 M malic acid, 0.1 M succinic acid, 4 wt% PEG 6000, pH 4.5
- ○ 0.02 M tartaric acid, 0.1 M succinic acid, 4 wt% PEG 6000, pH 4.5
- ▲ 0.02 M itaconic acid, 0.1 M succinic acid, 4 wt% PEG 6000, pH 4.5
- △ 0.02 M fumaric acid, 0.1 M succinic acid, 4 wt% PEG 6000, pH 4.5
- ■ 0.02 M maleic acid, 0.1 M succinic acid, 4 wt% PEG 6000, pH 4.5
- × 0.12 M succinic acid, 4 wt% PEG 6000, pH 4.5

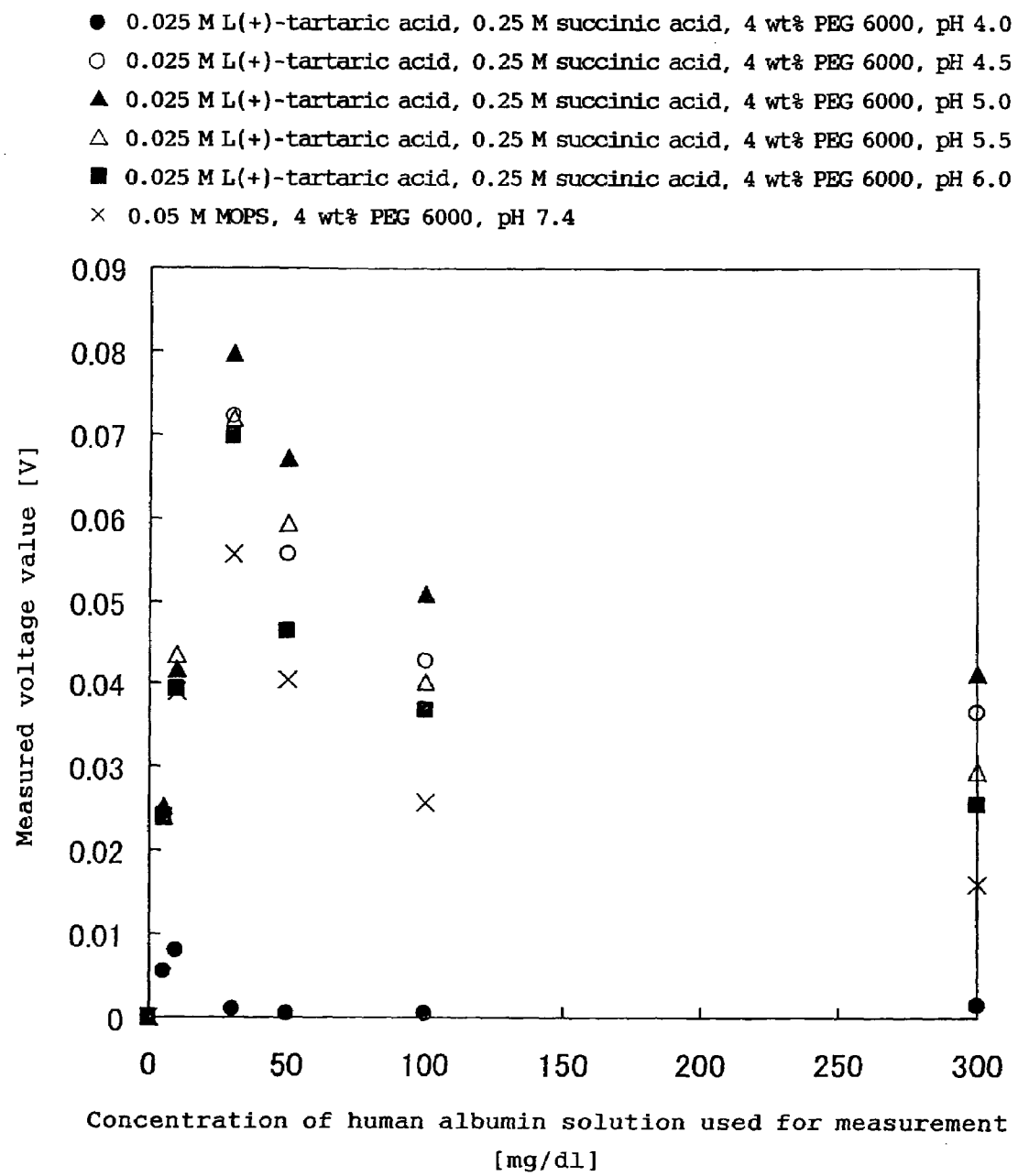

IMMUNOREACTION MEASUREMENT METHOD

RELATED APPLICATIONS

This is a US national phase filing under 35 U.S.C. § 371 of PCT/JP03/15754 filed Dec. 09, 2003 and claims priority from JP 2002-357459 filed Dec. 10, 2002 and JP 2002-364195 filed Dec. 16, 2002.

TECHNICAL FIELD

The present invention relates to an immunoreaction measurement method capable of measuring an antigen or antibody contained as a subject substance in a sample, and an immunoreaction measurement reagent for use in the method.

BACKGROUND ART

In order to diagnose various diseases and examine progression of disease conditions, a practice of measuring a content of protein which exists in human body fluid and is characteristic to each disease has been in wide use in the medical field.

For measurement of contents of such proteins, typically, immunoreaction measurement methods utilizing highly specific antigen-antibody reactions have been broadly used, and at present, immunoreaction measurement methods with various principles applied thereto have been developed and utilized.

Among them, measurement methods for detecting an agglutination complex generated by an antigen-antibody reaction, such as nephelometry, turbidimetry and slide agglutination, are well known. These methods are performed using a solution in which an antigen and antibody are uniformly dispersed, and therefore, are collectively called homogeneous immunoreaction measurement methods.

These reactions lead to generation of agglutination complexes, and a reaction solution becomes turbid depending on amounts of an antigen and antibody. Nephelometry and turbidimetry are methods of optically measuring the turbidity, and in nephelometry, turbidity is measured based on an amount of light scattered by a reaction system; in turbidimetry, turbidity is measured based on an amount of transmitted light reduced by scattering in a reaction system. In general, the same reaction solution (reaction system) can be used as subject substances of both the methods, and a subject which can be measured by the one method can also be measured by the other method.

Slide agglutination is a method for determining turbidity caused by generated agglutination complexes by visual observation on a slide glass or the like, and can employ the same reaction system as used for nephelometry and turbidimetry.

In the above-described conventional homogeneous immunoreaction measurement methods, various additives have been tested for accelerating an antigen-antibody reaction to measure a trace amount of component with high sensitivity. As a well-known example mentioned can be a method of improving reaction time and measurement sensitivity by allowing a water-soluble polymer, such as polyethylene glycol (PEG), dextran, polyvinylpyrrolidone or polyvinyl chloride, to coexist in a reaction system so as to accelerate formation of agglutination complexes due to an antigen-antibody reaction.

Among these water-soluble polymers, polyethylene glycol is known to have a high level of effect even at a relatively low concentration, and polyethylene glycol having an average molecular weight of 6000 has been widely used at a concentration of 2 to 6 wt %. Particularly, a 4 wt % concentration is believed to produce only a small level of non-specific turbidity, and thus highly effective.

The effect of accelerating an antigen-antibody reaction by a water-soluble polymer typically has a tendency to be large, as the molecular weight, or the concentration of the polymer in an aqueous solution to be used, is high. Concerning measurement of an antigen-antibody reaction, the higher the degree of an antigen-antibody reaction, i.e. the intensity of a signal depending on the concentration of an antigen, the more favorably the S/N ratio can be kept and the more stably the measurement can be performed. However, when an attempt is made to obtain the above-described effect by further acceleration of an antigen-antibody reaction, in the case of adding a conventional water-soluble polymer, a water-soluble polymer with a higher concentration or a higher molecular weight is required. This however leads to an increase in viscosity of a solution, in which such a water-soluble polymer is dissolved, raising a problem in that the solution is difficult to handle during manipulation for analysis.

In homogeneous immunoreaction measurement methods, a phenomenon called the zone phenomenon is generally known. The zone phenomenon refers to a phenomenon that, when an amount of one of an antigen and antibody exceeds the equivalent weight region thereof which forms the largest amount of agglutination complexes, generation of the agglutination complex becomes difficult. A binding reaction between a polyvalent antibody and a more than monovalent antigen is explained by the famous Heidelberger's lattice hypothesis, the details of which are described in Fundamental Immunology, William E. Paul, (1984) (Japanese language translation, Kiso Menekigaku, supervised by Tomio Tada, pp. 714–716 (1987)).

In actual homogeneous immunoreaction measurements, an antibody is often used to measure an antigen concentration. A measurement value often has a more important meaning when the antigen concentration is high than when it is low. Therefore, a zone phenomenon due to excess antigens may often cause problems. In regions other than a prozone, a huge molecular chain comprising a complex, in which antibodies and antigens are alternately linked together, is generated, and the amount or size of the molecular chain is increased depending on the antigen concentration if the antibody concentration is constant. Measurement of the amount or size of the molecular chain as optical variations allows quantitative determination of the antigen concentration. Further, since an antigen-antibody complex can be sufficiently observed even by naked eye as turbidity or agglutination s in a solution, depending on the concentrations of an antibody and antigen, the antigen concentration can be qualitatively determined by visual observation or the like.

However, in an antigen excess region, the presence of an antigen in an excessively larger amount than that of an antibody causes an increase in amount of the antibody whose binding site is saturated with the antigen. For this reason, generation of a molecular chain as described above becomes difficult, and the reaction result in this case cannot be readily distinguished from the reaction result in the case of a low antigen concentration. Accordingly, correct quantification and determination depending on the antigen concentration cannot be performed, raising a problem in that a concentration range to be measured has to be limited in order to avoid such a situation.

As measures for improving this zone phenomenon, the following measures have been proposed.

For example, in Japanese Laid-Open Patent Publication No. Hei 09-08984, a method is disclosed in which the concentration of sodium chloride is set to 20 to 250 g/L in a neutral condition of pH 6.0 to 8.0, to suppress an immunoreaction so as to measure a subject substance without dilution; in Japanese Laid-Open Patent Publication No. Hei 10-332694, a method is disclosed in which the concentration of sodium chloride is set to 10 to 250 g/L in an acidic condition of pH 3.5 to 5.5 or in an alkaline condition of pH 9.0 to 12.0, to suppress an immunoreaction so as to measure a subject substance without dilution. Japanese Laid-Open Patent Publication No. Hei 11-344494 proposes, for example, the following method. Namely, in an immunological agglutination reaction in which the concentration of sodium chloride is set to 0.05 to 0.08 M in a neutral condition of pH 7.4 and an insoluble support particle is bound to an antibody or antigen as the one subjected to an immunoreaction, at least one dicarboxylic acid, selected from the group consisting of a malic acid, a glutaric acid, an adipic acid, a succinic acid, the salts and esters of these acids, is added to a reaction system in an amount of 1 to 20 wt %.

However, there has been a problem in that in any of the methods described in these publications, a measurement value of an immunoreaction is decreased in a measurement region other than an antigen excess region.

In view of the above-described conventional problems, accordingly, an object of the present invention is to provide an immunoreaction measurement method capable of easily increasing accuracy of measurement values, and an immunoreaction measurement reagent for use in the method. Another object of the present invention is to provide an immunoreaction measurement method capable of relaxing a limitation of a measurement range due to a zone phenomenon that occurs in an antigen excess region, and an immunoreaction measurement reagent for use in the method.

DISCLOSURE OF INVENTION

The present invention relates to an immunoreaction measurement method for measuring an antigen or antibody contained as a subject substance in a sample, comprising the steps of:

(A) mixing into the sample at least one compound (hereinafter also referred to as "specific compound") selected from the group consisting of dicarboxylic acids having a hydroxyl group, dicarboxylic acids having a double bond, straight-chain dicarboxylic acids expressed by the chemical formula (1): $HOOC(CH_2)_nCOOH$ (n is an integer), and the salts of these dicarboxylic acids, and an antibody or antigen as a specifically binding substance capable of specifically binding to the subject substance, to obtain an acidic reaction solution; and (B) detecting in the reaction solution an antigen-antibody complex generated by an antigen-antibody reaction of the subject substance and the specifically binding substance.

It is preferable that the dicarboxylic acids having a hydroxyl group be a malic acid and a tartaric acid, and that the dicarboxylic acids having a double bond be an itaconic acid, a fumaric acid and a maleic acid.

It is preferable that a methylene chain of the straight-chain dicarboxylic acids have a length n of integer of 1 to 7.

It is preferable that the reaction solution be further added with a buffer.

It is preferable that the pH of the reaction solution be set to 4.0 to 6.0.

It is preferable that the pH of the reaction solution be set to 4.5 to 6.0.

Further, the pH of the reaction solution may be set to 4.5 to 5.0.

Further, the pH of the reaction solution may be set to 5.0 to 6.0.

It is preferable that the concentration of the specific compound in the reaction solution be set to not higher than 0.1 M.

Further, the concentration of the specific compound in the reaction solution may be set to the range of 0.01 M to 0.1 M.

The concentration of the specific compound in the reaction solution may be set to the range of 0.01 M to 0.05 M.

It is preferable that the reaction solution contain polyethylene glycol in an amount of not smaller than 2 wt % and not larger than 6 wt %.

It is preferable that the antigen-antibody complex be an agglutination complex.

It is preferable that, in the step (B), the agglutination complex be detected by measuring optical variations attributed to the agglutination complex.

It is preferable that the optical variations be variations in intensity of scattered light.

It is preferable that the specifically binding substance be an antibody comprising a monoclonal antibody.

It is also preferable that the specifically binding substance be a mixture of one sort or more of monoclonal antibodies having been prepared so as to be capable of generating an agglutination complex.

It is preferable that the antigen be human albumin.

Moreover, the present invention relates to an immunoreaction measurement reagent, containing at least one compound (specific compound) selected from the group consisting of dicarboxylic acids having a hydroxyl group, dicarboxylic acids having a double bond, straight-chain dicarboxylic acids expressed by the chemical formula (1): $HOOC(CH_2)_nCOOH$ (n is an integer), and the salts of these dicarboxylic acids, and an antibody or antigen as a specifically binding substance capable of specifically binding to the subject substance, the reagent being formulated such that the pH of a reaction solution becomes acidic when an antigen-antibody reaction occurs between the subject substance and the specifically binding substance.

Also in this case, it is preferable that the dicarboxylic acids having a hydroxyl group be a malic acid and a tartaric acid, and that the dicarboxylic acids having a double bond be an itaconic acid, a fumaric acid and a maleic acid.

It is preferable that a methylene chain of the straight-chain dicarboxylic acids have a length n of integer of 1 to 7.

It is preferable that the immunoreaction measurement reagent further comprise a buffer.

It is preferable that the immunoreaction measurement reagent have been formulated such that the pH of the reaction solution becomes 4.0 to 6.0. This pH may also be 4.5 to 6.0, 4.5 to 5.0, or 5.0 to 6.0.

It is preferable that the immunoreaction measurement reagent have been formulated such that the concentration of the specific compound in the reaction solution is not higher than 0.1 M.

It is also preferable that the immunoreaction measurement reagent have been formulated such that the concentration of the specific compound in the reaction solution becomes 0.01 M to 0.1 M.

It is further preferable that the immunoreaction measurement reagent have been formulated such that the concentration of the specific compound in the reaction solution becomes 0.01 M to 0.05 M.

It is preferable that the immunoreaction measurement reagent further contain polyethylene glycol, and that the concentration of the polyethylene glycol be not smaller than 2 wt % and not larger than 6 wt % when an antigen-antibody reaction occurs.

It is preferable that the specifically binding substance be an antibody comprising a monoclonal antibody.

It is preferable that the specifically binding substance be a mixture of one sort or more of monoclonal antibodies having been formulated so as to be capable of generating an agglutination complex.

It is preferable that the antigen be human albumin.

BRIEF DESCRIPTION OF DRAWINGS

FIG. 18 is a graph representing measurement results of immunoreactions in Example 8 of the present invention.

BEST MODE FOR CARRYING OUT THE INVENTION

Figure 1:
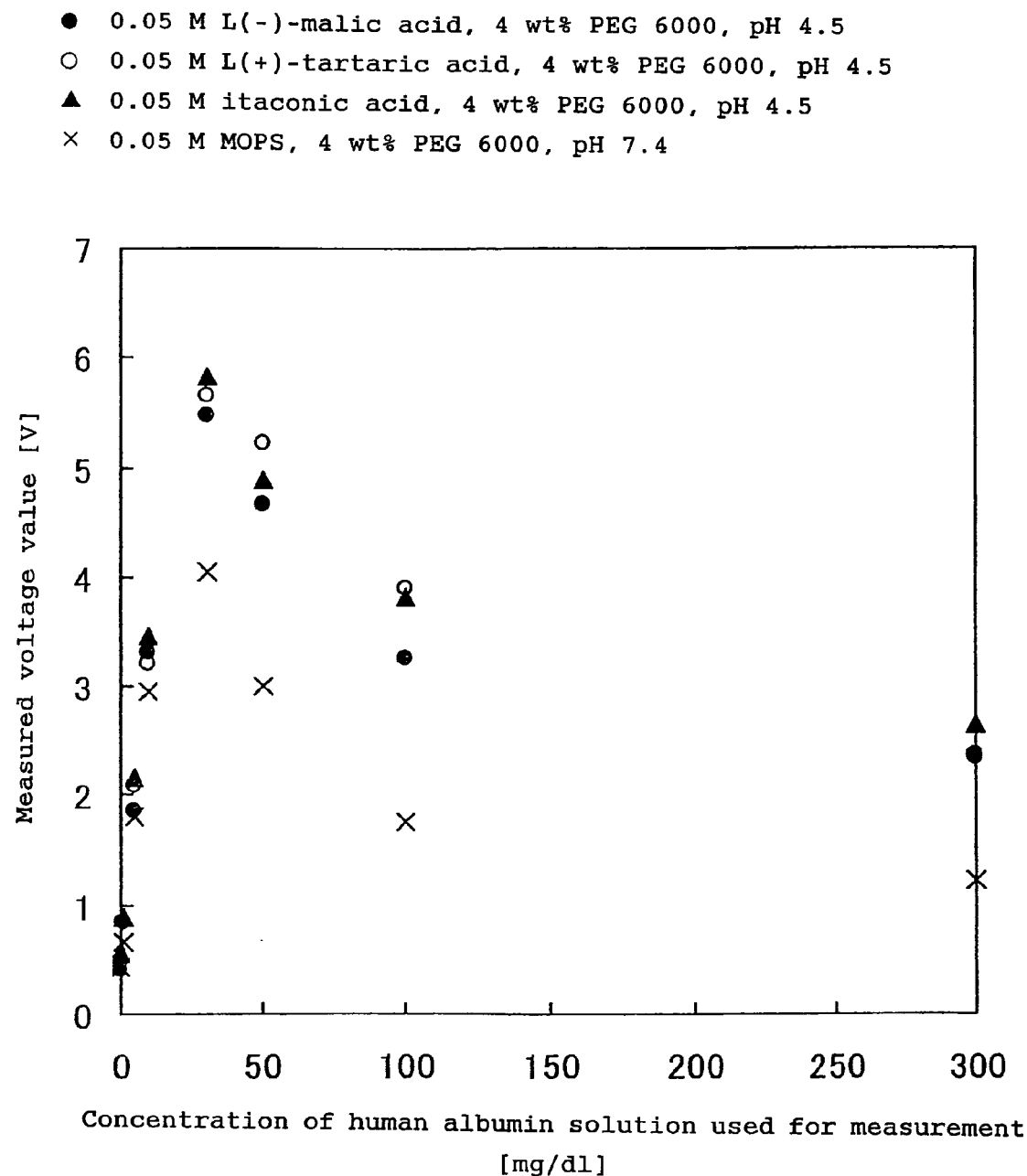
FIG. 1 is a graph representing measurement results of immunoreactions in Example 2 of the present invention.

The present invention relates to an immunoreaction measurement method capable of easily improving a measurement value and an immunoreaction measurement reagent for use in the method. In particular, the present invention relates to an immunoreaction measurement method capable of relaxing a limitation of a measurement range due to a zone phenomenon that occurs in an antigen excess region, and an immunoreaction measurement reagent for use in the method.

As a result of wholehearted efforts on their study, the present inventors found that a measurement value of an immunoreaction generated by binding of an antigen and antibody can be improved by mixing, with a reaction system, at least one compound (specific compound) selected from the group consisting of dicarboxylic acids having a hydroxyl group, dicarboxylic acids having a double bond, straight-chain dicarboxylic acids expressed by the chemical formula (1): $HOOC(CH_2)_nCOOH$ (n is an integer), and the salts of these dicarboxylic acids, to keep the reaction solution acidic, when an antigen-antibody reaction occurs. The present inventors also found that a limitation of a measurement range due to a zone phenomenon that occurs in an antigen excess region can be relaxed.

The following hypothesis can be made in terms of the above-described effects. In homogeneous immunoreaction measurements such as immunonephelometry and immunoturbidimetry, agglutination complexes are generated by an antigen-antibody reaction. This generation includes temporary agglutination by a specific antigen-antibody reaction, and secondary agglutination between agglutination complexes. It is thought that the above specific compound mainly acts for the secondary agglutination between agglutination complexes. It is generally known that, when an agglutination complex is regarded as a sort of colloid, the agglutination is accelerated by the function of ions. Since polyvalent carboxylic acid ion has a very strong function of coagulating colloid, it accelerates the secondary agglutination between complexes. However, as having high ion intensity, polyvalent carboxylic acid also exhibits the action of slightly inhibiting an antigen-antibody reaction.

In the acidic condition, since a dissociation rate of the carboxyl group in the above-described specific compound decreases, the ion intensity is lowered to reduce the action of inhibiting an antigen-antibody reaction, and the generation of agglutination complexes thus increases to make the secondary agglutination between agglutination complexes due to the agglutination action of colloid become significant. This allows the agglutination complex generating reaction to occur easily, which results in an improved measurement value. Further, a limitation of a measurement range due to a zone phenomenon that occurs in an antigen excess region is relaxed.

The immunoreaction measurement method in accordance with the present invention is an immunoreaction measurement method for measuring an antigen or antibody contained as a subject substance in a sample, the method comprising the steps of: (A) mixing into the sample at least one compound selected from the group consisting of dicarboxylic acids having a hydroxyl group, dicarboxylic acids having a double bond, straight-chain dicarboxylic acids expressed by the chemical formula (1): HOOC$(CH_2)_n$COOH (n is an integer), and the salts of these dicarboxylic acids, and an antibody or antigen as a specifically binding substance capable of specifically binding to the subject substance, to obtain an acidic reaction solution; and (B) detecting in the reaction solution an antigen-antibody complex generated by an antigen-antibody reaction of the subject substance and the specifically binding substance.

Herein, the reaction solution (reaction system) can include both the above-described acids and the salts thereof.

The specific compound provides the reaction solution with a buffering capability, and the reaction solution is set to be acidic. This eliminates the need for addition of another buffer to make the reaction solution acidic, and also allows effective exertion of the effect of improving a measurement value of the immunoreaction. This also enables effective exertion of the effect of relaxing a limitation of a measurement range due to a zone phenomenon that occurs in an antigen excess region. Of course, the reaction solution can further be added with a buffer.

The present invention also relates to a reagent for use in the above-described immunoreaction measurement method for measuring an antigen or antibody contained as a subject substance in a sample. Namely, the present invention relates to an immunoreaction measurement reagent, including the specific compound, and an antibody or antigen capable of specifically binding to a subject substance (specifically binding substance), wherein the reagent is formulated such that a reaction solution is acidic when an antigen-antibody reaction occurs between the subject substance and the specifically binding substance. Both of the above-described acids and the salts thereof may be contained in the reagent.

The specific compound provides the reagent with a buffering capability to, and the reagent is formulated such that a reaction solution becomes acidic when an antigen-antibody reaction occurs between a subject substance and a specific binding substance. This eliminates the need for addition of another buffer to make the reaction solution acidic, and also allows effective exertion of the effect of improving a measurement value of the immunoreaction. This also enables effective exertion of the effect of relaxing a limitation of a measurement range due to a zone phenomenon that occurs in an antigen excess region. The reagent can further include a buffer.

It is preferable that the concentration of the specific compound contained in the reaction solution be not lower than 0.01 M so that the reaction solution can obtain a sufficient buffering capability. Further, from the viewpoint of effectively exerting the effect of improving a measurement value as well as the effect of relaxing a limitation of a measurement range due to a zone phenomenon that occurs in an antigen excess region, the concentration is preferably not higher than 0.1 M. For satisfying both of these requirements, the concentration is preferably from 0.01 to 0.1 M, and more preferably from 0.01 to 0.05 M.

From the above reason, also in the case of using the immunoreaction reagent in accordance with the present invention, the concentration of the specific compound contained in the reaction solution is preferably not higher than 0.1 M, more preferably from 0.01 to 0.1 M, and further preferably from 0.01 to 0.05 M. The specific compound can be dissolved at such a concentration as showing a buffering capability against water, and the effect of improving a measurement value of an immunoreaction is large. Further, the effect of relaxing a limitation of a measurement range due to a zone phenomenon that occurs in an antigen excess region is large.

Herein, examples of dicarboxylic acids having a hydroxyl group, dicarboxylic acids having a double bond, straight-chain dicarboxylic acids expressed by the chemical formula (1): HOOC$(CH_2)_n$COOH (n is an integer), and the salts of these dicarboxylic acids may include: an L(−)-malic acid, D-malic acid, DL-malic acid, DL-sodium malate, L(−)-sodium malate, L(+)-tartaric acid, DL-tartaric acid, D(−)-tartaric acid, mesotartaric acid 1-hydrate, (+)potassium tartrate-water (2/1), (+)potassium sodium tartrate 4-hydrate, (+)ammonium tartrate, (+)potassium hydrogentartrate, (+)sodium hydrogentartrate 1-hydrate, (+)sodium tartrate 2-hydrate, itaconic acid, itaconic acid anhydrate, fumaric acid, monosodium fumarate, sodium fumarate, ferrous fumarate, maleic acid, maleic anhydride, sodium maleate, disodium maleate, malonic acid, sodium malonate, disodium malonate, thallium malonate, dithallium malonate, succinic acid, ammonium succinate, disodium succinate, glutaric acid, adipic acid, ammonium adipate, diammonium adipate, dipotassium adipate, pimelic acid, suberic acid, and azelaic acid, and these acids can be used singly or in combination of two or more of them.

As the dicarboxylic acids having a hydroxyl group, for example, a malic acid, a tartaric acid and the like are preferred. Among them, a tartaric acid is particularly preferred as being able to obtain, in a wider pH range, the effect of improving a measurement value of an immunoreaction generated by binding of an antigen and antibody and the effect of relaxing a limitation of a measurement range due to a zone phenomenon that occurs in an antigen excess region.

As the dicarboxylic acids having a double bond, for example, an itaconic acid, a fumaric acid and a maleic acid are preferred. Among them, an itaconic acid and a maleic acid are preferred because they have higher solubility so as to be able to readily stabilize a pH of a reaction solution. Moreover, an itaconic acid is particularly preferred as having a large effect of improving a measurement value of an immunoreaction generated by binding of an antigen and antibody, as well as a large effect of relaxing a limitation of a measurement range due to a zone phenomenon that occurs in an antigen excess region.

As the straight-chain dicarboxylic acids expressed by the chemical formula (1): HOOC$(CH_2)_n$COOH (n is an integer), one with a methylene chain having a length n of integer of 1 to 7 is preferred. Specifically, the preferable ones referred to with trivial names are: a malonic acid (n=1), a succinic acid (n=2), a glutaric acid (n=3), an adipic acid (n=4), a pimelic acid (n=5), a suberic acid (n=6), an azelaic acid (n=7), and the like. Among them, a malonic acid is especially preferred as being able to obtain, in a wider range of pH, the effect of improving a measurement value of an immunoreaction generated by binding between an antigen and antibody and the effect of relaxing a limitation of a measurement range due to a zone phenomenon that occurs in an antigen excess region.

As the buffer, those buffers known in the art can be used, which for example include: phosphate buffers such as monosodium dihydrogenphosphate and disodium hydrogenphosphate, sodium acetate, sodium cacodylate, and 2-(N-morpholino)ethanesulfonic acid.

In the case of using such a buffer, an amount of a buffer to be contained in the reaction solution may be appropriately adjusted according to the type of a buffer to be used, an amount of a sample (specimen) containing a subject substance, a method for supplying an antibody or antigen for an antigen or antibody as a subject substance in a reaction system, and the like, within the range where the effect of the present invention is not impaired.

In the immunoreaction measurement method of the present invention, the pH of the reaction solution is preferably set to 4.0 to 6.0. In this case, the specific compound exerts a large effect of improving a measurement value of an immunoreaction. It also exerts a large effect of relaxing a limitation of a measurement range due to a zone phenomenon that occurs in an antigen excess region. It is further preferable that the pH of the reaction solution be set to 4.5 to 6.0. The pH of the reaction solution may be set to 4.5 to 5.0, or 5.0 to 6.0.

The immunoreaction reagent in accordance with the present invention is preferably formulated such that the pH of the reaction solution becomes 4.0 to 6.0, and more preferably 4.5 to 5.0 or 5.0 to 6.0 when mixed with a reaction solution as an antigen-antibody reaction occurs.

Moreover, a reaction solution in the immunoreaction measurement method and the immunoreaction reagent in accordance with the present invention can be added with any other arbitrary component known in the art, according to the application, within the range where the effect of the present invention is not impaired. For example, when the present invention is applied to a homogeneous immunoreaction measurement method, such as nephelometry, turbidimetry or slide agglutination, polyethylene glycol (PEG) can be added to the reaction system and the immunoreaction reagent.

The amount of the component in the reaction solution in the immunoreaction measurement method of the present invention is preferably 2 to 6 wt %, and more preferably 4 wt %, from the viewpoint of leading to less non-specific agglutination and a large improvement in measurement sensitivity. Similarly, in the immunoreaction reagent of the present invention, the concentration of the component is preferably 2 to 6 wt %, and more preferably 4 wt %, when an antigen-antibody reaction occurs.

In order to reduce non-specific turbidity due to self-agglutination of an antigen or antibody, a surfactant, such as Tween 20, octylglucoside, sodium lauryl sulfate (SDS), sucrose monolaurate, or CHAPS, can be added to the reaction solution or the immunoreaction reagent. The surfactant is preferably contained in an amount not larger than 0.3 wt %, and more preferably not larger than 0.1 wt %, relative to the reaction solution in the immunoreaction measurement method in accordance with the present invention, as such a content leads to less inhibition of an antigen-antibody reaction.

Similarly, in the immunoreaction reagent in accordance with the present invention, the content thereof is preferably not larger than 0.3 wt %, and more preferably not larger than 0.1 wt %.

Measurement systems, to which the immunoreaction measurement method and the immunoreaction measurement reagent in accordance with the present invention are applied, are not particularly limited but are preferably homogeneous measurement systems such as nephelometry, turbidimetry and slide agglutination, which have a zone phenomenon that occurs in an antigen excess region, since they are expected to have the above-described effect of the present invention. In particular, nephelometry and turbidimetry, which have been widely used for measurement using omitted measurement apparatus, are preferred since steps required for determining a zone phenomenon that occurs in an antigen excess region can be removed or simplified.

In the immunoreaction measurement method in accordance with the present invention, the antigen-antibody complex is preferably an agglutination complex. In the step (B), the agglutination complex is preferably detected by measuring optical variations attributed to the agglutination complex. More preferably, the optical variations are variations in scattered light intensity or transmitted light amount. In particular, they are preferably variations in intensity of scattered light that sensitively responds to the size of the agglutination complex.

A sample to be used in the immunoreaction measurement method and the immunoreaction measurement reagent in accordance with the present invention can be any one containing an antigen or antibody as a subject substance, which can be exemplified by body fluid like urine or blood. Further, the antigen or antibody contained as a subject substance in the sample is not particularly limited, and may be any substance which can be measured generally using an antigen-antibody reaction. Examples thereof may include proteins, nucleic acids, lipids, bacteria, viruses and haptens. Among them, proteins, which are the major subject substances to be measured in clinical tests using an antigen-antibody reaction, are preferred.

Examples of proteins may include hormones, such as LH (luteinizing hormone), FSH (follicle-stimulating hormone), and hCG (human-chorionic gonadotropin), various immonoglobulin classes and the subclasses thereof, complement components, various markers for various infectious diseases, CRP, albumins, rheumatoid factors, and blood group antigens. Among them, human albumin is particularly preferred.

Dicarboxylic acids having a hydroxyl group, dicarboxylic acids having a double bond, straight-chain dicarboxylic acids expressed by the chemical formula (1): $HOOC(CH_2)_nCOOH$ (n is an integer), and the salts of these dicarboxylic acids, have a chelation action, the property of efficiently trapping bivalent and trivalent metal ions, such as $Ca^{2+}$ and $Fe^{3+}$ present in a reaction solution. It is therefore preferable that, when the antigen holds a metal ion in the molecular structure thereof, an antibody capable of specifically binding to an antigen still specifically binds to an antigen after the metal ions have been released from that antigen. In this case, even if an antigen is a substance, holding a metal ion in the molecular structure and capable of changing the molecular structure by release of the metal ion, the measurement can be measured.

Moreover, in the case where an antigen holds a metal ion in the molecular structure thereof and the molecular structure is changed by release of the metal ion, the same metal ion as those held in the antigen may be added to a reaction solution so as to be present in the reaction solution when an antigen-antibody reaction occurs. An amount of the metal ion added to the reaction solution may be determined based on the chelation ability or the concentration of dicarboxylic acids having a hydroxyl group, dicarboxylic acids having a double bond, straight-chain dicarboxylic acids expressed by the chemical formula (1): $HOOC(CH_2)_nCOOH$ (n is an integer), and the salts of these dicarboxylic acids, the metal ion holding ability of the antigen, or the like.

An antibody used in the immunoreaction measurement method and the immunoreaction measurement reagent in accordance with the present invention is not particularly limited, and may include an antibody of any type of IgG, IgM, IgE, IgA, and IgD as long as it is capable of specifically binding to an antigen. Among them, an IgG antibody is preferred as having less non-specific reactivity and being relatively often available commercially, and thus easily obtainable. Further, although the type of an animal from which an antibody is derived is not limited, an antibody derived from a rabbit, goat or mouse is preferred as being relatively easily obtainable and generally used.

As the specifically binding substance, either a polyclonal antibody or a monoclonal antibody may be applied. Namely, a polyclonal antibody and a monoclonal antibody can be used singly or in combination; however, a monoclonal antibody is more preferably used as being capable of eternally producing the same antibodies. Further, a mixture of one sort or more of monoclonal antibodies prepared so as to be capable of producing an agglutination complex is more preferred.

A monoclonal antibody is produced by a hybridoma cell strain. A hybridoma cell line is established by isolating and culturing a single cell from a multitude of fused cells, which have both an ability to produce an antibody and a strong ability to proliferate, and are obtained by fusing a B cell capable of producing an antibody and a myeloma cell. For this reason, antibodies produced by the hybridoma cell line all have the same properties. A hybridoma cell line has a strong proliferating ability and can be cryopreserved. If a hybridoma cell line is appropriately controlled, therefore, the cell line will not be exhausted, and by culturing a hybridoma cell line in a culture solution or an abdominal cavity and purifying it, antibodies having the same properties can be obtained perpetually.

On the other hand, polyclonal antibodies can be obtained by administering an antigen into an animal to allow a number of antibodies capable of binding to the antigen to appear in blood, and collecting and purifying the entirety or part of the blood. Therefore, the properties of the polyclonal antibody are dependent on the individual difference, feeding environment, conditions, or the like, of the animal, and hence it is difficult to continue to obtain antibodies having the same properties. Accordingly, the use of a monoclonal antibody makes it possible to consistently use antibodies having the same property. For this reason, the antibody as a reagent is stably supplied, and as a result, it becomes possible to increase the stability in results of immunoreaction measurement using an immunoreaction measurement method and an immunoreaction measurement reagent.

The requirement of a monoclonal antibody to be satisfied for constituting a specifically binding substance being capable of binding to an antigen so as to form an agglutination complex. That is, when an antigen is a substance having a plurality of binding sites to one sort of monoclonal antibody, an agglutination complex can be generated by the one sort of monoclonal antibody. However, when an antigen is a substance having just one binding site to one sort of monoclonal antibody (first monoclonal antibody), at least two sorts of monoclonal antibodies need to be used. The requirement of a second monoclonal antibody is being capable of binding to the other site of an antigen so as to generate, together with the first monoclonal, an agglutination complex antibody when the antigen was bound to the antibody.

One example of the immunoreaction measurement method in accordance with the present invention is shown below.

Firstly, at least one compound selected from the group consisting of dicarboxylic acids having a hydroxyl group, dicarboxylic acids having a double bond, straight-chain dicarboxylic acids expressed by the chemical formula (1): $HOOC(CH_2)_nCOOH$ (n is an integer), and the salts of these dicarboxylic acids, is added to a buffer comprising a buffer such that a below-described reaction solution is made acidic, preferably at a pH set to 4.0 to 6.0.

One of a dispersion or solution and a sample (specimen) containing an antibody or antigen for an antigen or antibody as a subject substance is mixed with the buffer, and the other of the dispersion or solution and the sample is mixed to the resultant buffer to prepare a reaction solution, and an immunoreaction generated in the reaction solution is measured.

Herein, the concentration of the compound in the reaction solution may be arbitrary so long as it is within the range where the effect of improving a measurement value and the effect of relaxing a limitation of a measurement range due to a zone phenomenon that occurs in an antigen excess region are observed. The concentration of the compound is preferably not higher than 0.1 M, preferably from 0.01 to 0.1 M and further preferably from 0.01 to 0.05 M. The compound may also serve as a buffer.

A method of adding the specific compound, a method of adding a buffer to the reaction solution so as to keep the pH thereof acidic, and a method of adjusting the pH of the reaction solution, are not limited to the above-described methods. For example, the specific compound and the buffer may be previously present in a solution containing an antibody or antigen for an antigen or antibody as a subject substance in such a manner as to satisfy the above-described requirements.

One example of methods for preparing the immunoreaction reagent in accordance with the present invention is described below.

When an antigen or antibody for an antigen or antibody as a subject substance is adjusted separately from the specific compound, the antigen or antibody and the specific compound may be respectively prepared as follows. A solution containing an antigen or antibody for an antigen or antibody as a subject substance may have an arbitrary composition so long as the effect of the specific compound is obtained.

A solution containing the above compound is preferably prepared such that a pH of a reaction solution becomes 4.0 to 6.0 so as to be allowed to have a buffering capability necessary for maintaining the reaction solution acidic in an antigen-antibody reaction. Further, the concentration of the specific compound in the reaction solution may be arbitrary so long as it is within the range where the effect of improving a measurement value and the effect of relaxing a limitation of a measurement range due to a zone phenomenon that occurs in an antigen excess region can be obtained. A mixture obtained by mixing the buffer with the specific compound is added with pure water to adjust the concentration of the specific compound preferably to not higher than 0.1 M, more preferably to 0.01 to 0.1 M, and further preferably to 0.01 to 0.05 M. If the above-described requirements are satisfied, the buffer and the specific compound may be present in separate solutions. The specific compound itself may serve as the buffer.

The specific compound may be present in a solution containing an antibody or antigen for an antigen or antibody as a subject substance. In this case, the specific compound may be added to a solution containing an antibody or antigen for an antigen or antibody as a subject substance by subjecting the solution to dialysis or gel filtration, using a solution containing the specific substance prepared in such a manner as to satisfy the above-described requirements, so as to exchange low molecular weight components.

As described above, according to the immunoreaction measurement method and the immunoreaction measurement reagent in accordance with the present invention, at least one compound selected from the group consisting of dicarboxylic acids having a hydroxyl group, dicarboxylic acids having a double bond, straight-chain dicarboxylic acids expressed by the chemical formula (1): $HOOC(CH_2)_nCOOH$ (n is an integer), and the salts of these dicarboxylic acids, is caused to be present in an reaction system for an immunoreaction, to make the reaction system acidic, whereby it is possible to improve a measurement value of an immunoreaction generated by binding between an antigen and antibody. Furthermore, it is possible to relax a limitation of a measurement range due to a zone phenomenon that occurs in an antigen excess region.

In conventional methods of adding a water-soluble polymer, a water-soluble polymer has to be added at a high concentration, or a water-soluble polymer having a high molecular weight has to be added, in order to improve a measurement value and keep a better S/N ratio to perform stable measurement in measurement of an antigen-antibody reaction. This causes an increase in viscosity of the solution, thereby making it difficult to handle the solution for analysis and manipulation. As opposed to this, since the specific compound used in the present invention is a low-molecular-weight substance, the viscosity of the solution is low, and hence the solution is easy to handle for analysis and manipulation.

Further, since a limitation of a measurement range due to a zone phenomenon that occurs in an antigen excess region is relaxed to reduce a decrease in measurement value when the concentration of a subject substance is high, a region, where a measurement value is high and a sample is determined to be positive, can be broadened, thereby enlarging the range of measurable concentrations.

Hereinafter, examples of the present invention are specifically described, but the present invention is not limited to these examples. Although not shown in the following examples, an antibody may be immobilized on a fine particle carrier, such as a latex, a gold colloid, or a magnetic fine particle. It may alternately be labeled with an enzyme, a dye, a fluorescent substance, a luminescent substance, or the like.

Moreover, in the present invention, a buffer and pH of an antibody solution are not particularly limited. For example, when one-component reagent is constituted, in order to allow the antibody solution to contain at least one compound selected from the group consisting of dicarboxylic acids having a hydroxyl group, dicarboxylic acids having a double bond, straight-chain dicarboxylic acids expressed by the chemical formula (1): $HOOC(CH_2)_nCOOH$ (n is an integer), and the salts of these dicarboxylic acids, and to keep the pH of a reaction system in an acidic region, dialysis may be performed using an acidic buffer containing the above specific compound.

Furthermore, although NaOH was used for pH adjustment in the following examples, a hydroxide such as KOH, LiOH, $NH_4OH$, $Ca(OH)_2$ or $Mg(OH)_2$ may be used. Further, although an L(-)-malic acid, an L(+)-tartaric acid, an itaconic acid, a malonic acid, a succinic acid, a glutaric acid, an adipic acid, a pimelic acid, a suberic acid and an azelaic acid were used in the following examples for adjustments of ten sorts of buffers containing the specific compound, compounds other than those described above as the specific compounds may also be employed.

As for pH adjustment using a plurality of specific compounds, HCl or the like may be used when a pH after the compound has been dissolved in pure water is more alkaline than an aimed pH, or the above-described hydroxide or the like may be used when the pH is more acidic than an aimed pH. Further, the pH may be adjusted by adjusting a mixing ratio of the specific compounds.

EXAMPLE 1

In the present example, an immunoreaction was measured using an antibody solution usable in measurement employing slide agglutination, turbidimetry or nephelometry, and a reagent including a buffer which contained at least one compound selected from the group consisting of dicarboxylic acids having a hydroxyl group, dicarboxylic acids having a double bond, straight-chain dicarboxylic acids expressed by the chemical formula (1): $HOOC(CH_2)_nCOOH$ (n is an integer), and the salts of these dicarboxylic acids.

It is to be noted that pure water filtered with Milli-Q SP TOC (manufactured by Millipore) was used to prepare a buffer or the like described below. Any reagents, such as salts and buffers, which are not particularly described, were obtained from Wako Pure Chemical Industries. Polyethylene glycol (PEG) 6000 used here was an extra pure reagent, and other reagents used were guaranteed reagents.

(1) Preparation for Antibody Solution

As for antibody solutions prepared were a solution using a rabbit antihuman albumin polyclonal antibody and a solution where three sorts of mouse antihuman albumin monoclonal antibodies were mixed.

Firstly, an antibody solution using a rabbit antihuman albumin polyclonal antibody was prepared as follows. A rabbit antihuman albumin polyclonal antibody was purified by protein A column chromatography from antiserum, which was collected from rabbits immunized with human albumin. As protein A immobilized gel filled in a column, a gell obtained from Amersham-Pharmacia was used. As an equilibration buffer used for purification, a buffer at pH 8.9, containing 1.5 M of glycine and 3.0 M of sodium chloride, was used. As an elution buffer, a buffer at pH 4.0, containing 0.1 M of a citric acid, was used.

Purification was performed as follows. An equilibration buffer in a volume five times greater than the volume of the gel filled in the column was passed through the column to equilibrate the column. Then, an antiserum containing antibodies in an amount of 10 to 20% of the overall binding capacity of the column was double diluted with the equilibration buffer, and passed through the column to allow the antibodies in the serum to bind to protein A. Subsequently, the equilibration buffer was kept being passed until serum components incapable of being adsorbed to protein A did not come out of the column, and the column was then washed.

The elution buffer was passed through the column to elute antibodies bound to protein A. The eluted antibody fraction was placed in dialysis tube with a molecular weight cut off of 10000, and dialysis was performed several times using an about 100-fold volume of buffer of pH 7.4, containing 0.05 M of 3-(N-morpholino)propanesulfonic acid (manufactured by Dojin, hereinafter expressed by MOPS), 0.15 M of sodium chloride and 0.04 wt % of $NaN_3$, to substitute components in the buffer.

Thereafter, the antibody concentration was estimated based on measurement of absorbance at 280 nm, and the antibody concentration was adjusted with the same buffer as used in the dialysis to 3.0 mg/ml, to obtain an antibody solution.

Next, an antibody solution where three sorts of mouse antihuman albumin monoclonal antibodies were mixed was prepared as follows.

As mouse antihuman albumin monoclonal antibodies, a monoclonal antibody, produced by a cell strain (National Institute of Bioscience and Human-Technology, National Institute of Advanced Industrial Science and Technology, deposit number: FERM BP-7938, hereinafter expressed by the 7938 strain), and FU-301 and FU-303, produced by Nippon Biotest Laboratories inc., were used. As the monoclonal antibody produced by the 7938 strain, one obtained by purifying ascites fluid of a mouse with the protein A column chromatography, as above described. When each monoclonal antibody was mixed in the antibody solution, the amounts of the monoclonal antibodies produced by 7938 strain, FU-301 and FU-303 were all 0.0333 mg/ml, and the monoclonal antibodies were mixed such that the amount of the final concentration of a total monoclonal antibody in the antibody solution was about 0.1 mg/ml.

It should be noted that the concentration and the mixing ratio of each antibody solution prepared above are not limited thereto. Further, although a prepared antibody solution can be preserved at room temperature, it is preferably preserved at low temperature, and more preferably at 4° C., in terms of preventing denaturalization of the antibody.

(2) Preparation of Buffer

For the buffer, ten sorts of compounds shown below were used.

As the dicarboxylic acid having a hydroxyl group, an L(−)-malic acid or an L(+)-tartaric acid was used; as the dicarboxylic acid having a double bond, an itaconic acid was used; as the straight-chain dicarboxylic acids expressed by the chemical formula (1): $HOOC(CH_2)_nCOOH$ (n is an integer), a malonic acid (n=1), a succinic acid (n=2), a glutaric acid (n=3), an adipic acid (n=4), a pimelic acid (n=5), a suberic acid (n=6) and an azelaic acid (n=7) were used.

A buffer containing an L(−)-malic acid was prepared as follows. An L(−)-malic acid and polyethylene glycol 6000 were weighed so as to have final concentrations of 0.05 M and 4 wt %, respectively, and an L(−)-malic acid and polyethylene glycol 6000 were added with and dissolved in pure water in a volume corresponding to about 90% of a volume of a buffer to be finally obtained. An aqueous NaOH solution was added to the resultant solution to adjust the pH to 4.5, and the resultant solution was added with pure water to prepare a solution having an aimed volume so as to obtain a buffer.

A buffer containing an L(+)-tartaric acid was prepared as follows. An L(+)-tartaric acid and polyethylene glycol 6000 were weighed so as to have final concentrations of 0.05 M and 4 wt %, respectively, and a L(+)-tartaric acid and polyethylene glycol 6000 were added with and dissolved in pure water in a volume corresponding to about 90% of a volume of a buffer to be finally obtained. An aqueous NaOH solution was added to the resultant solution to adjust the pH to 4.5, and the resultant solution was added with pure water to prepare a solution having an aimed volume so as to obtain a buffer.

A buffer containing an itaconic acid was prepared as follows. An itaconic acid and polyethylene glycol 6000 were weighed so as to have final concentrations of 0.05 M and 4 wt %, respectively, and an itaconic acid and polyethylene glycol 6000 were added with and dissolved in pure water having a volume corresponding to about 90% of a volume of a buffer to be finally obtained. An aqueous NaOH solution was added to the resultant solution to adjust the pH to 4.5, and the resultant solution was added with pure water to prepare a solution having an aimed volume so as to obtain a buffer.

A buffer containing a malonic acid was prepared as follows. A malonic acid and polyethylene glycol 6000 were weighed so as to have final concentrations of 0.05 M and 5 wt %, respectively, and a malonic acid and polyethylene glycol 6000 were added with and dissolved in pure water having a volume corresponding to about 90% of a volume of a buffer to be finally obtained. An aqueous NaOH solution was added to the resultant solution to adjust the pH to 5.0, and the resultant solution was added with pure water to prepare a solution having an aimed volume so as to obtain a buffer.

A buffer containing a succinic acid was prepared as follows. A succinic acid and polyethylene glycol 6000 were weighed so as to have final concentrations of 0.05 M and 5 wt %, respectively, and a succinic acid and polyethylene glycol 6000 were added with and dissolved in pure water having a volume corresponding to about 90% of a volume of a buffer to be finally obtained. An aqueous NaOH solution was added to the resultant solution to adjust the pH to 5.0, and the resultant solution was added with pure water to prepare a solution having an aimed volume so as to obtain a buffer.

A buffer containing a glutaric acid was prepared as follows. A glutaric acid and polyethylene glycol 6000 were weighed so as to have final concentrations of 0.05 M and 5 wt %, respectively, and a glutaric acid and polyethylene glycol 6000 were added with and dissolved in pure water having a volume corresponding to about 90% of a volume of a buffer to be finally obtained. An aqueous NaOH solution was added to the resultant solution to adjust the pH to 5.0, and the resultant solution was added with pure water to prepare a solution having an aimed volume so as to obtain a buffer.

A buffer containing an adipic acid was prepared as follows. An adipic acid and polyethylene glycol 6000 were weighed so as to have final concentrations of 0.05 M and 5 wt %, respectively, and an adipic acid and polyethylene glycol 6000 were added with and dissolved in pure water having a volume corresponding to about 90% of a volume of a buffer to be finally obtained. An aqueous NaOH solution was added to the resultant solution to adjust the pH to 5.0, and the resultant solution was added with pure water to prepare a solution having an aimed volume so as to obtain a buffer.

A buffer containing a pimelic acid was prepared as follows. A pimelic acid and polyethylene glycol 6000 were weighed so as to have final concentrations of 0.05 M and 5 wt %, respectively, and a pimelic acid and polyethylene glycol 6000 were added with and dissolved in pure water having a volume corresponding to about 90% of a volume of a buffer to be finally obtained. An aqueous NaOH solution was added to the resultant solution to adjust the pH to 5.0, and the resultant solution was added with pure water to prepare a solution having an aimed volume so as to obtain a buffer.

A buffer containing a suberic acid was prepared as follows. A suberic acid and polyethylene glycol 6000 were weighed so as to have final concentrations of 0.05 M and 5 wt %, respectively, and a suberic acid and polyethylene glycol 6000 were added with and dissolved in pure water having a volume corresponding to about 90% of a volume of a buffer to be finally obtained. An aqueous NaOH solution was added to the resultant solution to adjust the pH to 5.0, and the resultant solution was added with pure water to prepare a solution having an aimed volume so as to obtain a buffer.

A buffer containing an azelaic acid was prepared as follows. An azelaic acid and polyethylene glycol 6000 were weighed so as to have final concentrations of 0.05 M and 5 wt %, respectively, and an azelaic acid and polyethylene glycol 6000 were added with and dissolved in pure water having a volume corresponding to about 90% of a volume of a buffer to be finally obtained. An aqueous NaOH solution was added to the resultant solution to adjust the pH to 5.0, and the resultant solution was added with pure water to prepare a solution having an aimed volume so as to obtain a buffer. It is to be noted that each buffer obtained above was preserved at room temperature.

EXAMPLE 2

In the present example, the effect of the present invention using an acidic reaction system containing at least one compound selected from the group consisting of dicarboxylic acids having a hydroxyl group, dicarboxylic acids having a double bond, straight-chain dicarboxylic acids expressed by the chemical formula (1): $HOOC(CH_2)_nCOOH$ (n is an integer), and the salts of these dicarboxylic acids, on an antigen-antibody reaction, was compared with the effect in the case of a neutral reaction system generally used in an immunoreaction measurement method. The comparison with the conventional method was made by measuring human albumin as the subject substance, using immunonephelometry.

As the reagent used was one obtained by mixing each buffer containing an L(−)-malic acid, an L(+)-tartaric acid or an itaconic acid with the antibody solution including a rabbit antihuman albumin polyclonal antibody, as in Example 1.

Further, as a buffer for comparison which formed a neutral reaction system, a buffer of pH 7.4, containing 0.05 M of MOPS and 4 wt % of polyethylene glycol 6000, was used. As the antibody solution, the same one as described above was used.

As the sample used were an antigen solution obtained by dissolving, in a PBS buffer containing 0.04 wt % of $NaN_3$ (containing 8 g/L of NaCl, 0.2 g/L of KCl, 1.15 g/L of $Na_2HPO_4.12H_2O$ and 0.2 g/L of $KH_2PO_4$, pH 7.4), human albumin (manufactured by Wako Pure Chemical Industries) as an antigen at the concentration of 0, 1, 5, 10, 30, 50, 100 or 300 mg/dl.

It should be noted that the antibody solutions and the samples (antigen solutions) were preserved at 4° C. before use, and each buffer was preserved at room temperature.

As the measurement device used was as follows. A semiconductor laser pointer (manufactured by Kikoh Giken Kabushiki Kaisya, model number: MLXS-D-12-680-35), having a wavelength of 680 nm modulated at 270 Hz and an output power of about 15 mW, was used as a light source. A visible and infrared light precision measurement silicon photodiode (manufactured by Hamamatsu Photonics K. K., model number: S2387-66R) was used as a detector. A cell was constructed by attaching optical glass plates having a thickness of 0.1 cm together, which was in the shape of a square prism having a volume of about 200 µl.

The cell was disposed 0.5 cm away from the light source, one side of the cell being perpendicular to the light source. The detector was disposed 5.5 cm away from the cell and at an angle of 90 degrees with respect to the light source. A light shielding tube was placed between the detector and the cell so as to prevent stray light from entering the detector. A current signal depending on the amount of light detected by the detector was amplified by a current-voltage conversion circuit ($10^6$ V/A) and an operational amplifier to a 100-fold voltage signal. Thereafter, the voltage signal was passed through a lock-in amplifier (manufactured by NF Corporation, model number: 5610B) to perform phase-sensitive detection and then input into a computer by GPIB control.

As for each buffer, the human albumin solution having each of the above concentrations was measured as follows. A reaction solution was obtained by mixing 178 µl of the buffer, 9 µl of the human albumin solution, and 7 µl of the antibody solution. Namely, in the reaction solution, the final concentration of the antibody was about 0.11 mg/ml, and the final concentration of human albumin was equivalent to one obtained by multiplying the concentration of the human albumin solution used in measurement by 0.046.

Firstly, the buffer and the human albumin solution having the above-described volumes were added to the cell, followed by mixing by stirring. Subsequently, the antibody solution having the above-described volume was added to the cell, followed by mixing by stirring, causing an antigen-antibody reaction, while obtaining a reaction solution. Measurement of intensity of scattered light was started 10 seconds before the addition of the antibody solution, and was continued every 0.5 seconds for 300 seconds. Measurement values were obtained as voltage values. An influence of contamination of the cell on measurement was removed by compensating the measurement values based on measurement performed such that pure water was placed in the cell before measuring each reaction. The measurement values obtained at respective times over 200 to 300 seconds were averaged, and the resultant average value was regarded as a measurement value for the human albumin solution having each concentration. The measurement was performed at room temperature (about 20° C.).

FIG. 1 shows the measurement results. Shown in FIG. 1 were plots representing results of measurement of the human albumin solution having each concentration up to 300 mg/dl with respect to each buffer. The vertical axis represents a voltage value while the horizontal axis represents the concentration of the human albumin solution used for the measurement. It is to be noted that each plotted value was obtained by subtracting a measurement value obtained when a buffer did not contain human albumin (0 mg/dl), from a measurement value of the human albumin solution having each concentration with respect to the same buffer. It indicates that the higher the measured voltage value, the larger the amount of scattered light entering the detector, indicating the higher turbidity of a reaction system and the larger amount of an antigen-antibody complex generated by an antigen-antibody reaction.

It was found from FIG. 1 that higher measurement values were obtained in using each buffer of the present example (●, ○, ▲ in FIG. 1) than in using the buffer of the comparative example (X in FIG. 1). Further, in using the buffer of the comparative example (X), the measurement value decreased due to a zone phenomenon that occurred in an antigen excess region with a peak of 30 mg/dl.

Similarly, in using each buffer using 0.05 M of an L(−)-malic acid, 0.05 M of an L(+)-tartaric acid or 0.05 M of an itaconic acid (●, ○, ▲ in FIG. 1), the measurement value showed a tendency to decrease due to a zone phenomenon that occurred in an antigen excess region with a peak of 30 mg/dl. It was however found that, with the measurement value improved, it was possible to perform the measurement without the influence of the decrease in measurement value due to a zone phenomenon that occurred in an antigen excess region, in a wider antigen concentration range.

According to the measurement results of the present example, in the case of the buffer containing MOPS as the comparative example (X in FIG. 1), the measurement was possible without considering the influence of the decrease in measurement value due to a zone phenomenon that occurred in an antigen excess region, in the concentration range of the human albumin solution up to 50 mg/dl. As opposed to this, in the case of each buffer using an L(−)-malic acid, an L(+)-tartaric acid or an itaconic acid (●, ○, ▲ in FIG. 1), the measurement was possible without considering the influence of a zone phenomenon that occurred in an antigen excess region in the concentration range of the human albumin solution up to about 100 mg/dl, and it was hence found that the measurable concentration range in this case was wider than that in the case of the comparative example.

EXAMPLE 3

In the present example, in the same manner as in Example 2 above, the effect of an acidic reaction system containing at least one compound selected from the group consisting of dicarboxylic acids having a hydroxyl group, dicarboxylic acids having a double bond, straight-chain dicarboxylic acids expressed by the chemical formula (1): $HOOC(CH_2)_nCOOH$ (n is an integer), and the salts of these dicarboxylic acids, on an antigen-antibody reaction, was examined comparing with the effect in the case of a neutral reaction system generally used in an immunoreaction measurement method. The comparison with the conventional method was made by measuring human albumin as the subject substance, using immunonephelometry.

As the reagent used was one obtained by combining each buffer containing a malonic acid, a glutaric acid, an adipic acid, a pimelic acid, a suberic acid or an azelaic acid, with the antibody solution including a rabbit antihuman albumin polyclonal antibody, as in Example 1. Further, one obtained by combining a buffer containing a succinic acid with the antibody solution including a mouse antihuman albumin monoclonal antibody, as in Example 1, was used.

As a comparative example, a buffer of pH 7.4, containing 0.05 M of MOPS and 4 wt % of polyethylene glycol 6000, was used for forming a neutral reaction system. As the antibody solution, one including a rabbit antihuman albumin polyclonal antibody was used when compared with each buffer containing a malonic acid, a glutaric acid, an adipic acid, a pimelic acid, a suberic acid or an azelaic acid; the antibody solution including a mouse antihuman albumin monoclonal antibody was used when compared with the buffer containing a succinic acid.

As for the human albumin solution, which was the antigen solution used as the sample, was one obtained by dissolving, in Nagahama's control urine (dissolved in distilled water so as to contain 10 g/L of uria, 10 g/L of NaCl, 0.5 g/L of creatinine and 0.2 g/L of acetone), human albumin at the concentration of 0, 5, 10, 30, 50, 100 or 300 mg/dl. It should be noted that the antibody solution and the sample (antigen solution) were preserved at 4° C. before use, and each buffer was preserved at room temperature.

As the measurement device used was as follows. The device used was theoretically the same as, but structurally different from, the device in Example 2. A semiconductor laser pointer having a wavelength of 785 nm modulated at 270 Hz and an output power of about 20 mW (manufactured by Kikoh Giken Kabushiki Kaisya, model number: MLXS-D-12-785-70) was used as a light source. A visible and infrared light precision measurement silicon photodiode (manufactured by Hamamatsu Photonics K. K., model number: S2387-66R) was used as a detector. A cell was constructed by attaching optical glass plates having a thickness of 0.1 cm together, which was in the shape of a square prism, having a volume of about 600 µl.

The cell was disposed 1 cm away from the light source, one side of the cell being perpendicular to the light source. The detector was disposed 1 cm away from the cell and at an angle of 90 degrees with respect to the light source. A light shielding tube was placed between the detector and the cell so as to prevent stray light from entering the detector. A current signal depending on the amount of light detected by the detector passed through a current-voltage conversion circuit ($10^6$ V/A) and then a lock-in amplifier (manufactured by NF Corporation, model number: 5610B), to perform phase-sensitive detection and input into a computer by GPIB control.

As for each buffer, the human albumin solution with each concentration was measured as follows. 534 µl of the buffer, 27 µl of the human albumin solution and 21 µl of the antibody solution were mixed to obtain a reaction solution. Namely, in the reaction solution, the final concentration of the antibody was equivalent to one obtained by multiplying the concentration of the antibody solution used in measurement by about 0.036, and the final concentration of human albumin was equivalent to one obtained by multiplying the concentration of the human albumin solution used in measurement by about 0.046.

Firstly, the buffer and the human albumin solution having the above-described volumes were added to the cell, followed by mixing by stirring. Thereafter, the antibody solution having the above-described volume was added to the cell, followed by mixing by stirring, causing an antigen-antibody reaction. Measurement of intensity of scattered light was started 7 minutes after the addition of the antibody solution, and was continued every 1 second for 10 seconds. The measurement values were obtained as voltage values. An influence of contamination of the cell on measurement was removed by compensating the measurement values based on measurement which had been performed, where pure water was placed in the cell before measuring each reaction. The measurement values as thus obtained were averaged, and the resultant average value was regarded as a measurement value for a human albumin solution having each concentration. The measurement was performed at room temperature (about 20° C.).

Figure 2:
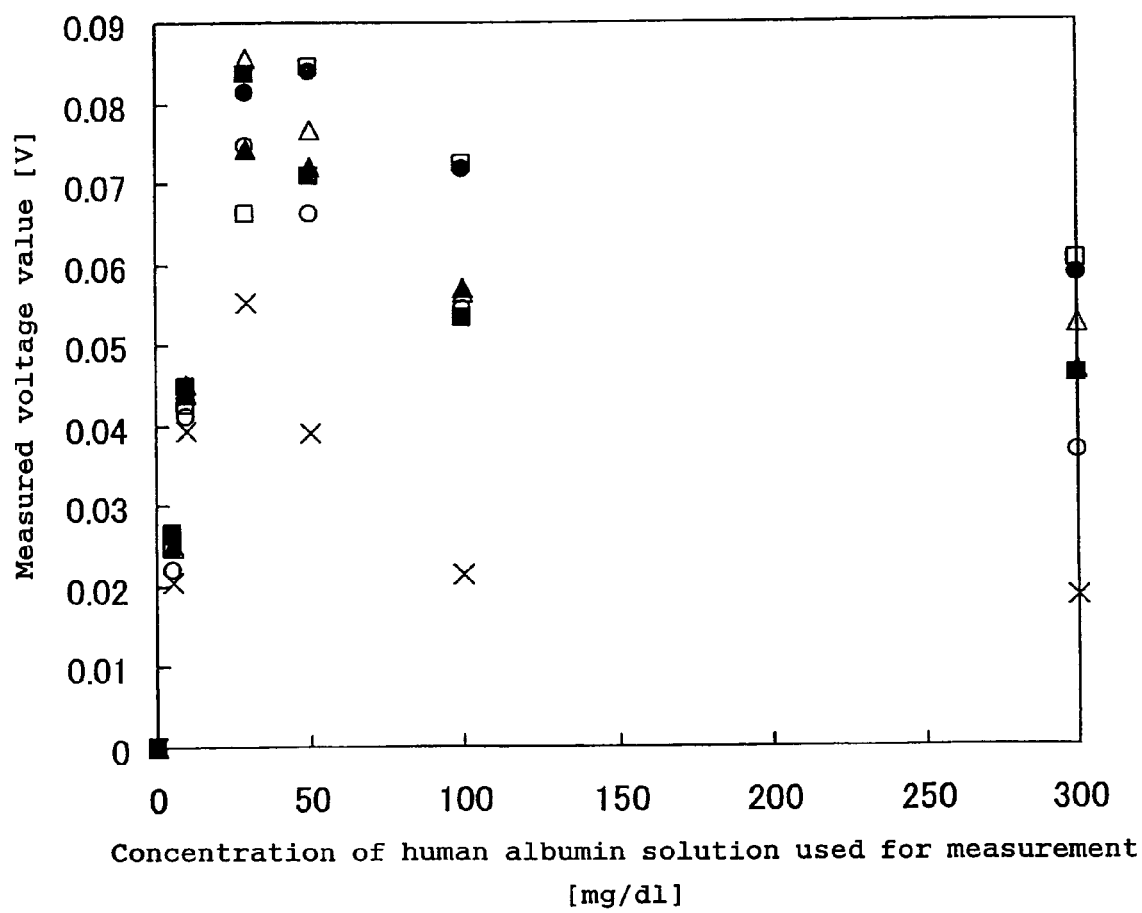
FIG. 2 is a graph representing measurement results of immunoreactions using reagents containing a malonic acid or the like in Example 3 of the present invention.
Figure 3:
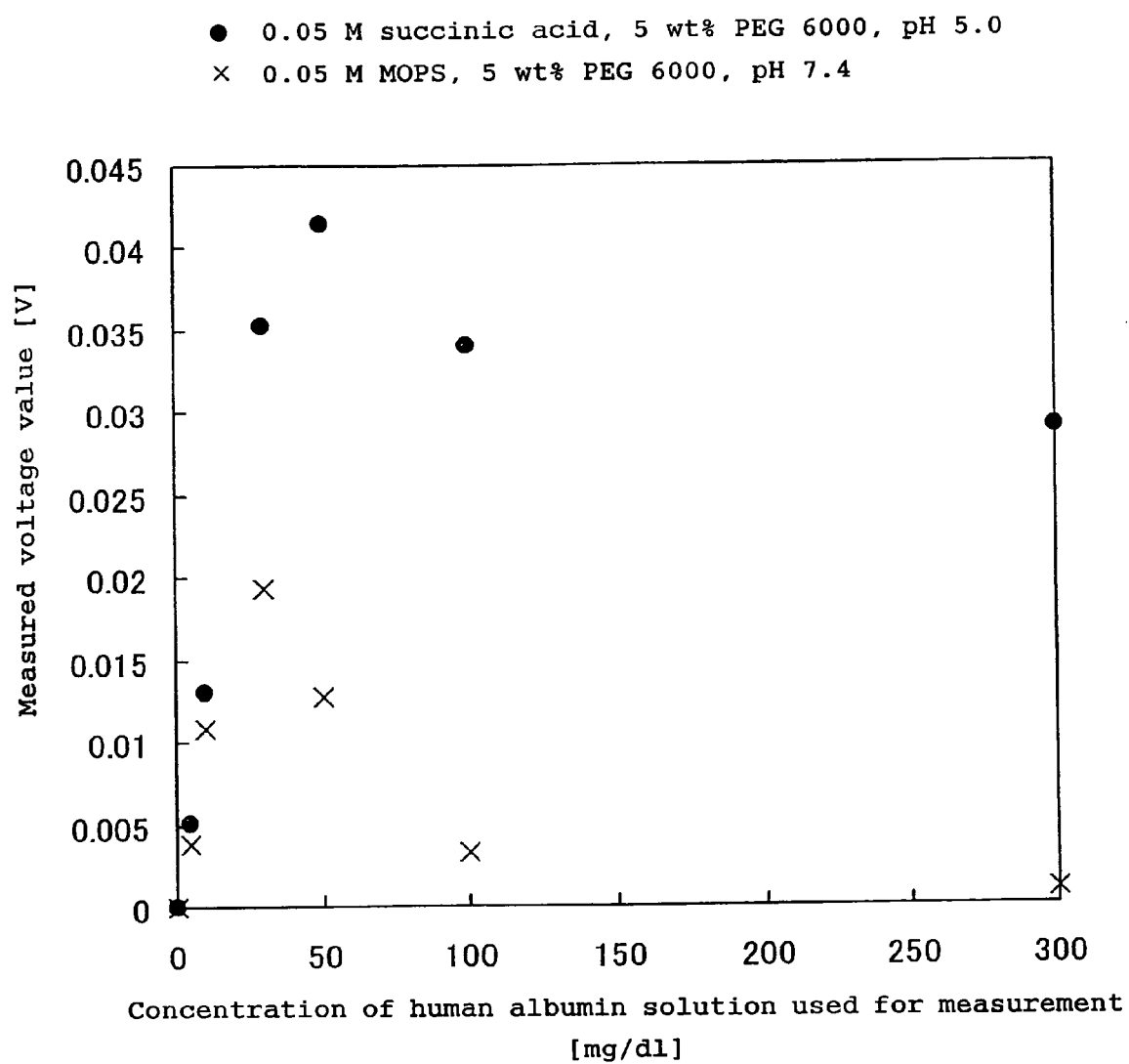
FIG. 3 is a graph representing measurement results of immunoreactions using reagents containing a succinic acid in Example 3 of the present invention.

FIGS. 2 and 3 show the measurement results. Shown in FIGS. 2 and 3 were plots representing results of measurement of the human albumin solution having each concentration up to 300 mg/dl, using each buffer containing a malonic acid (●), a glutaric acid (○), an adipic acid (▲), a pimelic acid (△), a suberic acid (■) or an azelaic acid (□), and the antibody solution including a rabbit antihuman albumin polyclonal antibody. The vertical axis represents a voltage value while the horizontal axis represents the concentration of the human albumin solution used for the measurement. It is to be noted that each plotted value was obtained by subtracting a measurement value, obtained when a buffer did not contain human albumin (0 mg/dl), from a measurement value of the human albumin solution having each concentration with respect to the same buffer.

It was found from FIG. 2 that higher measurement values were obtained in using each buffer of the present example (●, ○, ▲, △, ■, □ in FIG. 2) than in using the buffer (buffer of pH 7.4, containing 0.05 M of MMOPS and 5 wt % of polyethylene glycol) of the comparative example (X in FIG. 2), except for the blank value (when the human albumin concentration was 00 mg/dl). Further, in each case, the measurement value showed a tendency to decrease due to a zone phenomenon that occurred in an antigen excess region. It was however found from FIG. 3 that, for the same reason as in Example 2, the measurement was possible without the influence of the decrease in measurement value due to a zone phenomenon that occurred in an antigen excess region, in a wider antigen concentration range than that in the comparative example.

FIG. 3 shows plots representing results of measurement of the human albumin solution having each concentration up to 300 mg/dl, using the buffer containing a succinic acid and the antibody solution including a mouse antihuman albumin monoclonal antibody (●). It was found from FIG. 3 that higher measurement values were obtained in using the buffer containing a succinic acid of the present example (●) than in using the buffer of the comparative example (X). Further, in each case, the measurement value showed a tendency to decrease due to a zone phenomenon that occurred in an antigen excess region. It was found that, for the same reason as in Example 2, the measurement was possible without the influence of the decrease in measurement value due to a zone phenomenon that occurred in an antigen excess region, in a wider antigen concentration range.

As thus described, it was confirmed from FIGS. 2 and 3 that the immunoreaction measurement method in accordance with the present invention allows improvement in measurement value of an antigen-antibody reaction. It was also confirmed that the method allows relaxing of a limitation of a measurement range due to a zone phenomenon that occurs in an antigen excess region.

It was further confirmed that the use of the immunoreaction reagent in accordance with the present invention allows improvement in measurement value of an antigen-antibody reaction. It was also confirmed that the use of the reagent allows relaxing of a limitation of a measurement range due to a zone phenomenon that occurs in an antigen excess region.

It should be noted that the order of mixing the antigen solution, the buffer and the sample is not particularly limited, and the mixing ratio can be determined according to a measurement range of a necessary antigen concentration.

Further, in the above measurement, the mixture of the reagent and the sample were mixed and, therefore, a larger degree of a buffer, an additive such as polyethylene glycol 6000, and at least one compound selected from the group consisting of dicarboxylic acids having a hydroxyl group, dicarboxylic acids having a double bond, straight-chain dicarboxylic acids expressed by the chemical formula (1): $HOOC(CH_2)_nCOOH$ (n is an integer), and the salts of these dicarboxylic acids were diluted more than before the mixing. However, when the concentration before the dilution was different from the concentration after the dilution by up to about 10%, the obtained measurement result was much the same as a measurement result expected based on the concentration before the dilution, and hence the influence of the dilution was almost zero. In order to prevent concentration variations due to dilution, it was possible to prepare a mixture such that the concentration of each substance when mixed in a reagent became an aimed concentration, in consideration of dilution by the mixing.

EXAMPLE 4 pH dependencies of effects on an antigen-antibody reaction, respectively exhibited by a dicarboxylic acid having a hydroxyl group, a dicarboxylic acid having a double bond, and a straight-chain dicarboxylic acid expressed by the chemical formula (1): $HOOC(CH_2)_nCOOH$ (n is an integer), were examined using immunonephelometry.

In the present example, dicarboxylic acids having a hydroxyl group and a dicarboxylic acid having a double bond were studied. As the dicarboxylic acids having a hydroxyl group, an L(−)-malic acid and an L(+)-tartaric acid were used; as a dicarboxylic acid having a double bond, an itaconic acid was used. As the subject substance, human albumin was used. As the human albumin solution as the sample, the same one as in Example 2 was used. As the antibody solution, the antibody solution including a rabbit antihuman albumin polyclonal antibody, as in Example 1, was used.

For examining the pH dependency in using the dicarboxylic acids having a hydroxyl group, each buffer of pH 4.0, 4.5 or 5.0, containing 0.05 M of an L(−)-malic acid and 4 wt % of polyethylene glycol 6000, was prepared. Further, each buffer of pH 4.0, 4.5 or 5.0, containing 0.05 M of an L(+)-tartaric acid and 4 wt % of polyethylene glycol 6000, was prepared.

For examining the pH dependency in using the dicarboxylic acid having a hydroxyl group, each buffer of pH 4.0, 4.5 or 5.0, containing 0.05 M of an itaconic acid and 4 wt % of polyethylene glycol 6000, was prepared.

Moreover, as a comparative example, a buffer of pH 7.4, containing 0.05 M of MOPS and 4 wt % of polyethylene glycol 6000, was used; as for the antibody solution, the same antibody solution as above, including a rabbit antihuman albumin polyclonal antibody, was used.

The immunoreaction measurement was performed in the same manner as in Example 2.

Figure 4:
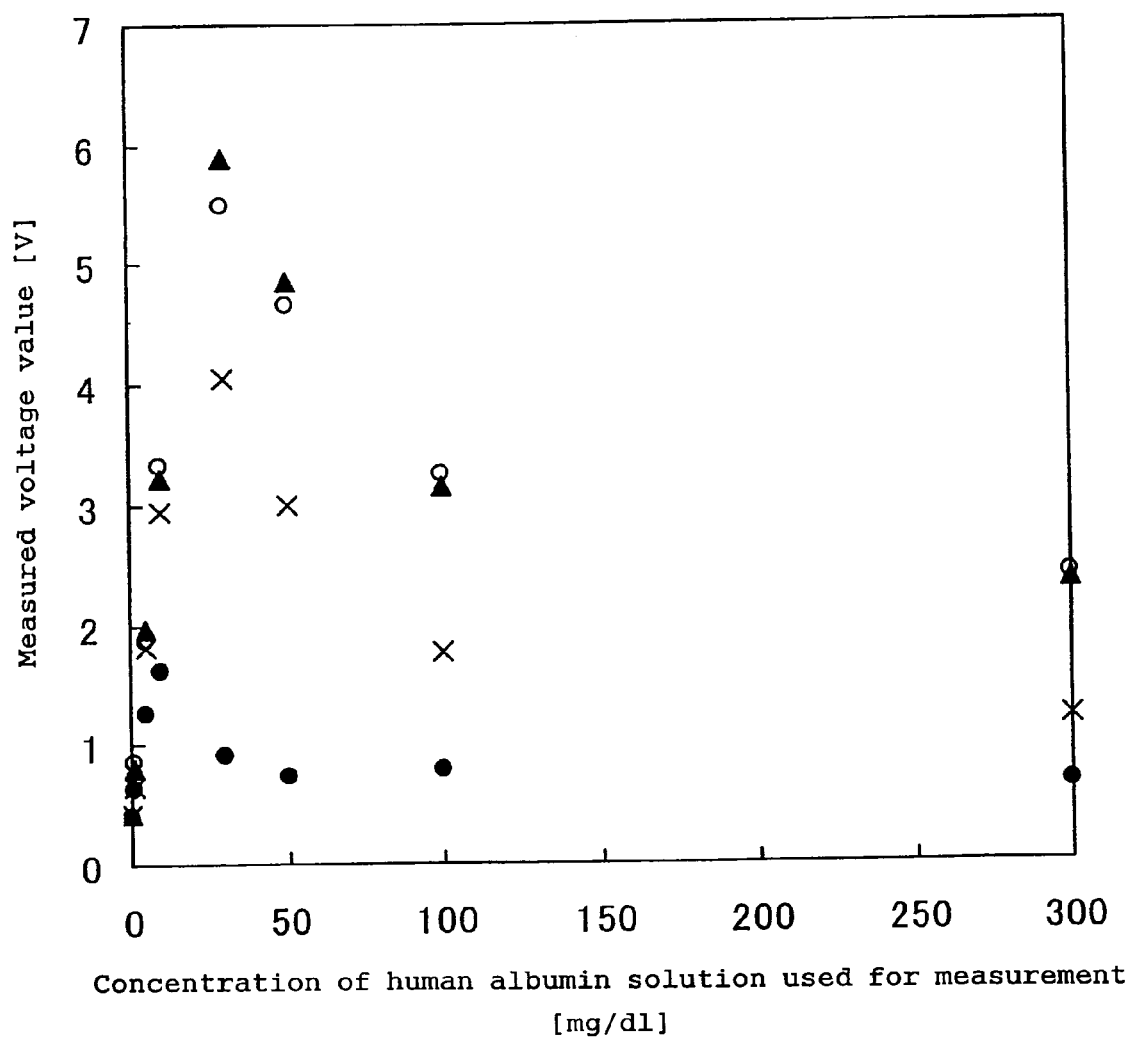
FIG. 4 is a graph representing measurement results of immunoreactions using reagents containing an L(-)-malic acid in Example 4 of the present invention.
Figure 5:
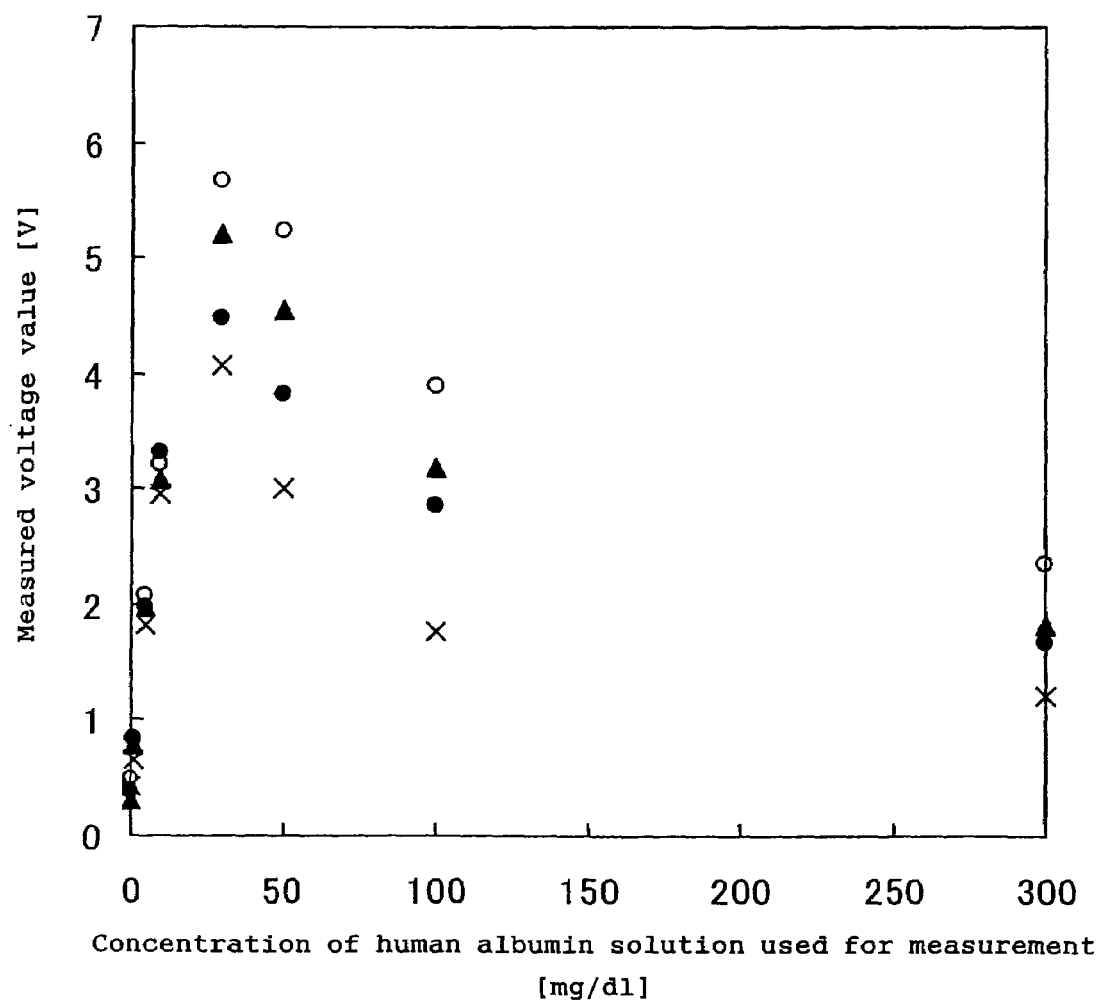
FIG. 5 is a graph representing measurement results of immunoreactions using reagents containing an L(+)-tartaric acid in Example 4 of the present invention.
Figure 6:
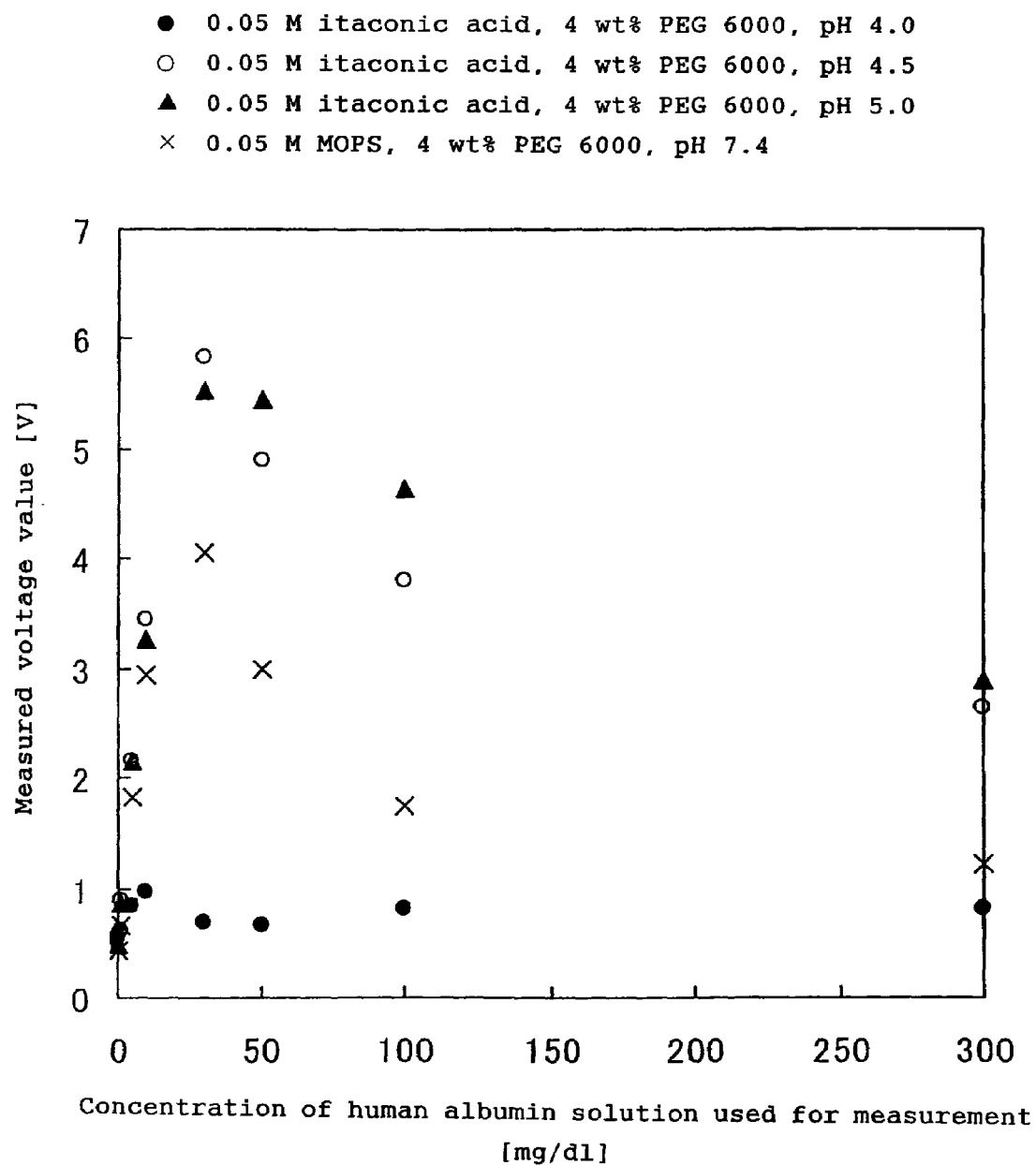
FIG. 6 is a graph representing measurement results of immunoreactions using reagents containing an itaconic acid in Example 4 of the present invention.
Figure 7:
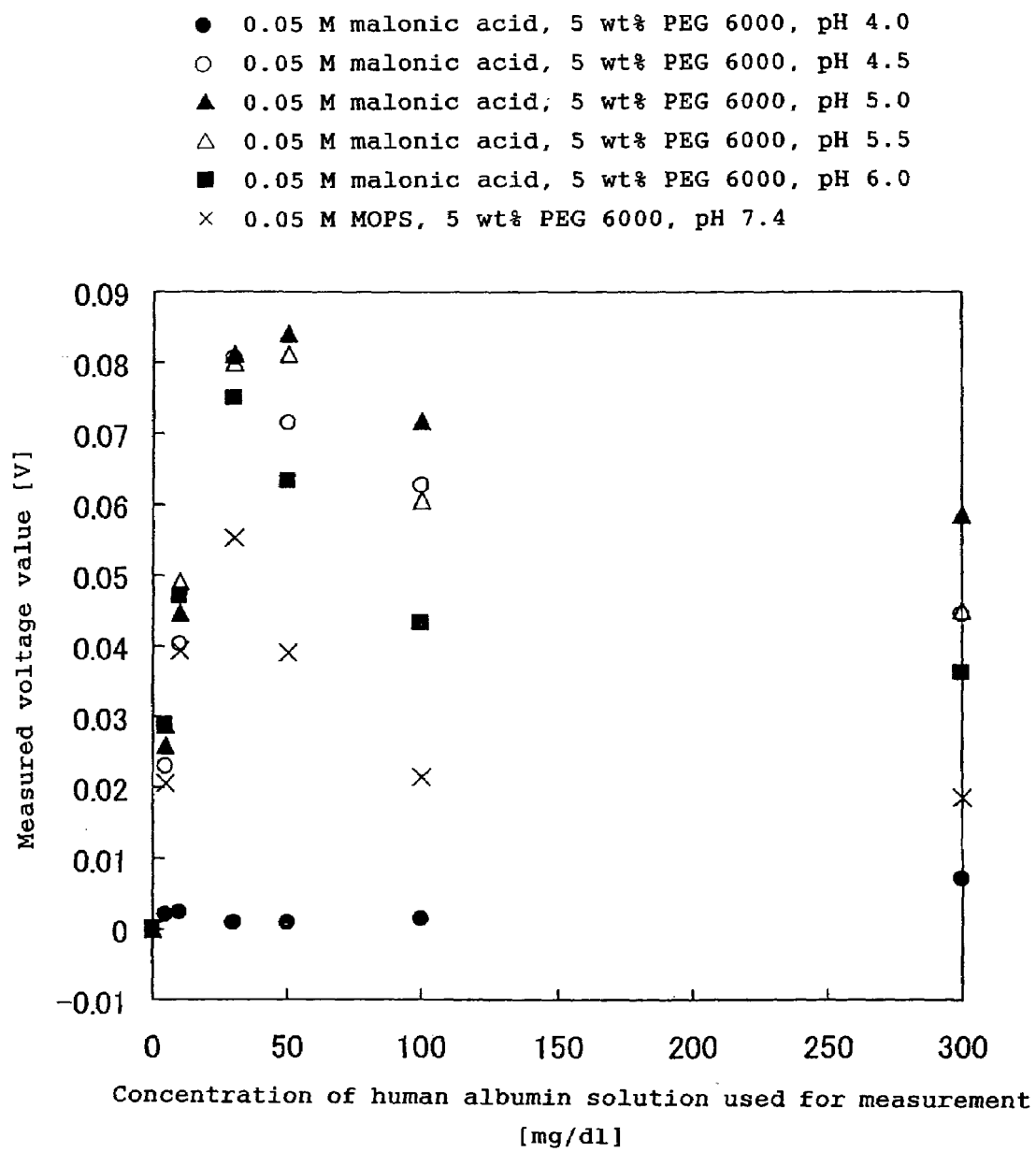
FIG. 7 is a graph representing measurement results of immunoreactions using reagents containing a malonic acid in Example 5 of the present invention.
Figure 8:
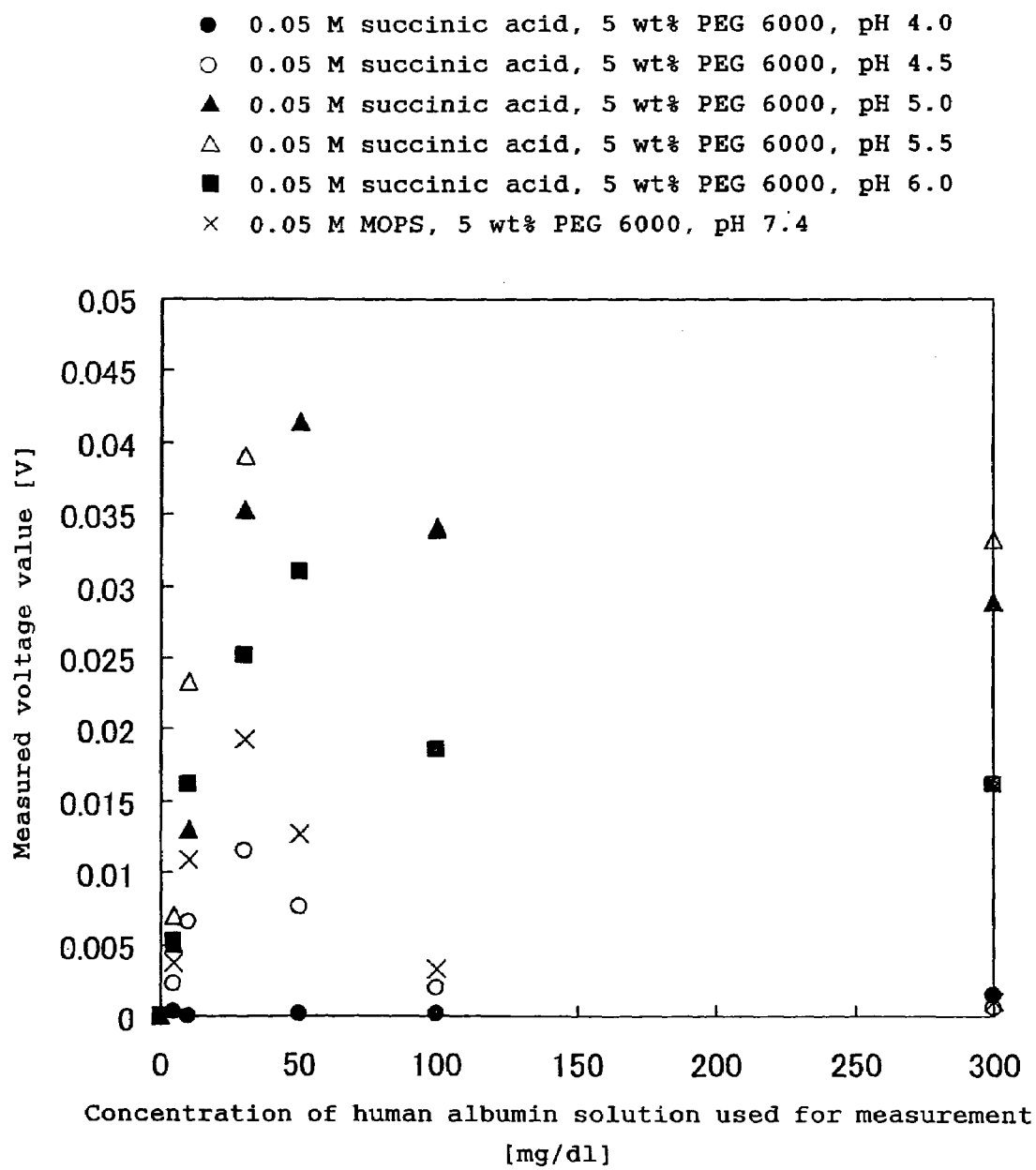
FIG. 8 is a graph representing measurement results of immunoreactions using reagents containing a succinic acid in Example 5 of the present invention.
Figure 9:
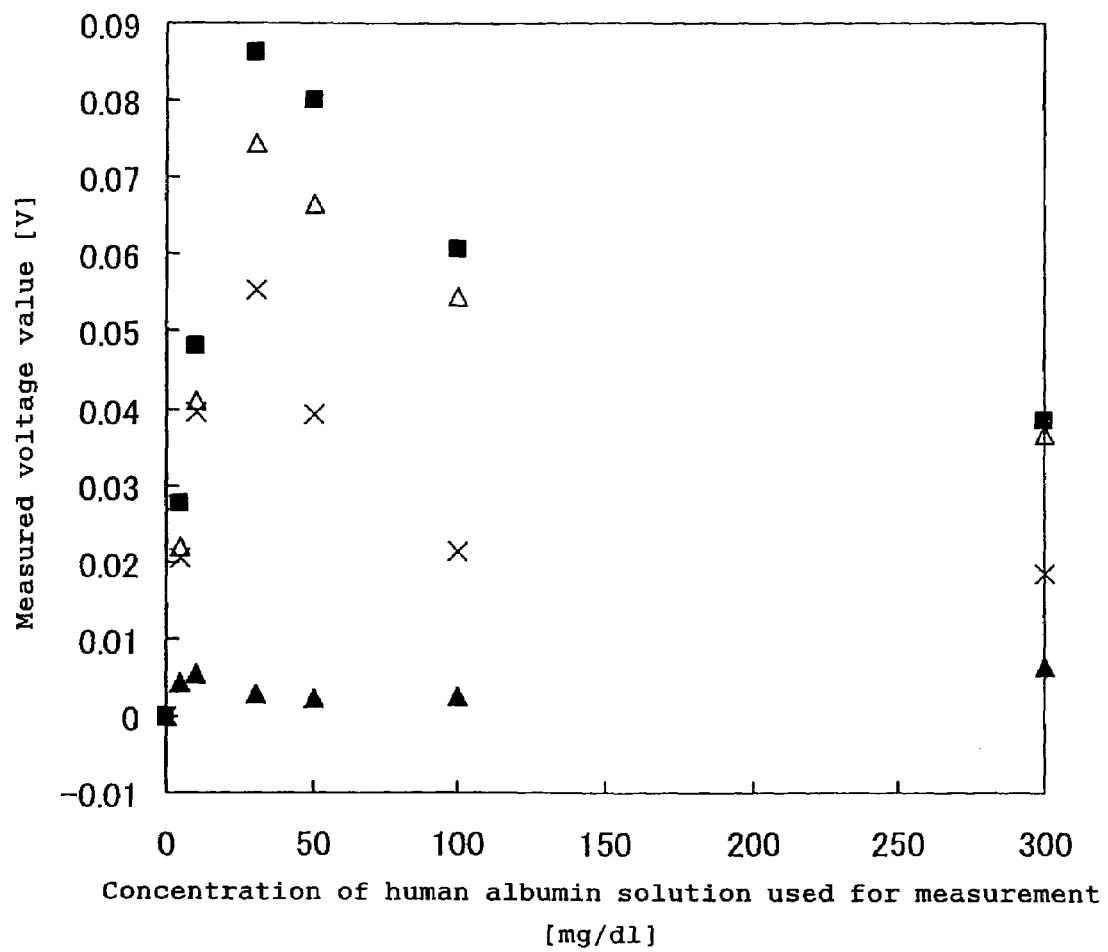
FIG. 9 is a graph representing measurement results of immunoreactions using reagents containing a glutaric acid in Example 5 of the present invention.
Figure 10:
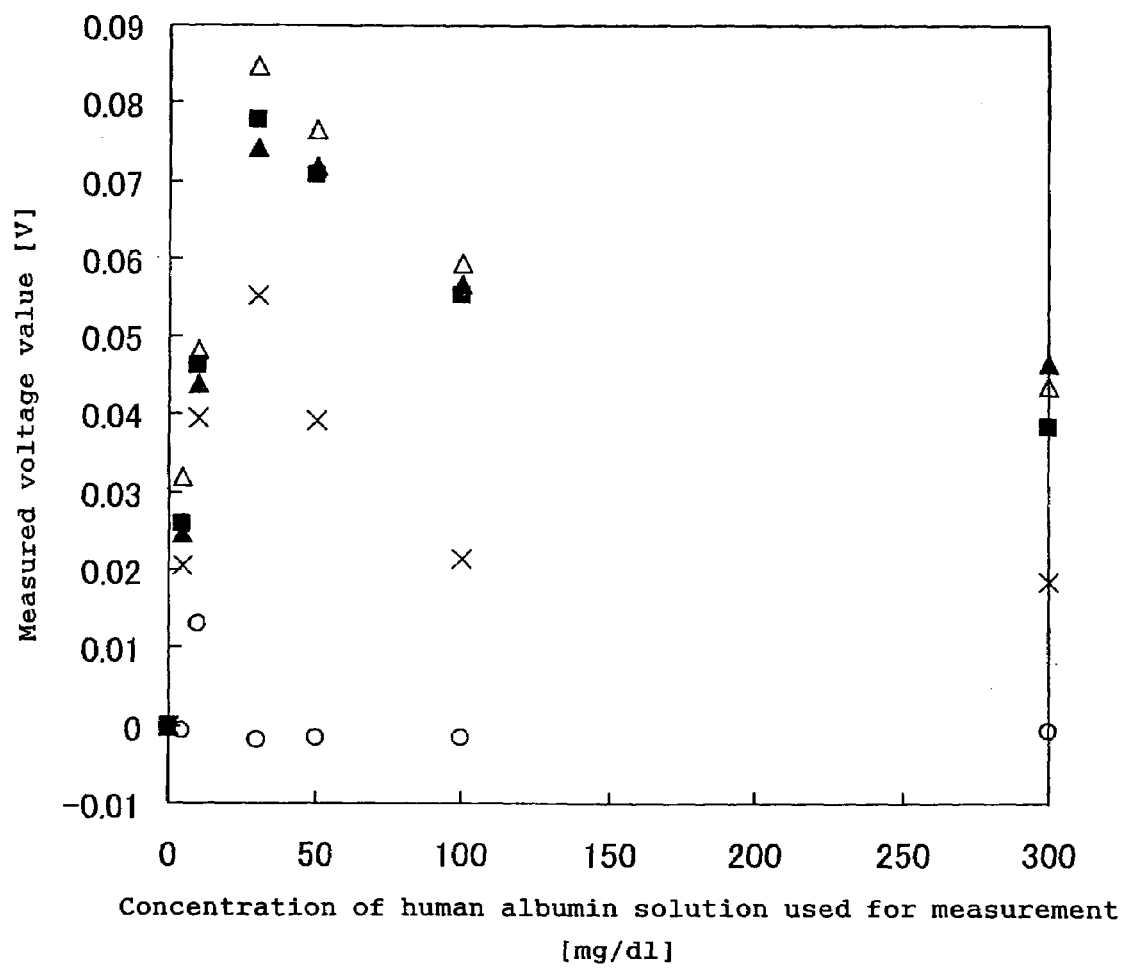
FIG. 10 is a graph representing measurement results of immunoreactions using reagents containing an adipic acid in Example 5 of the present invention.
Figure 11:
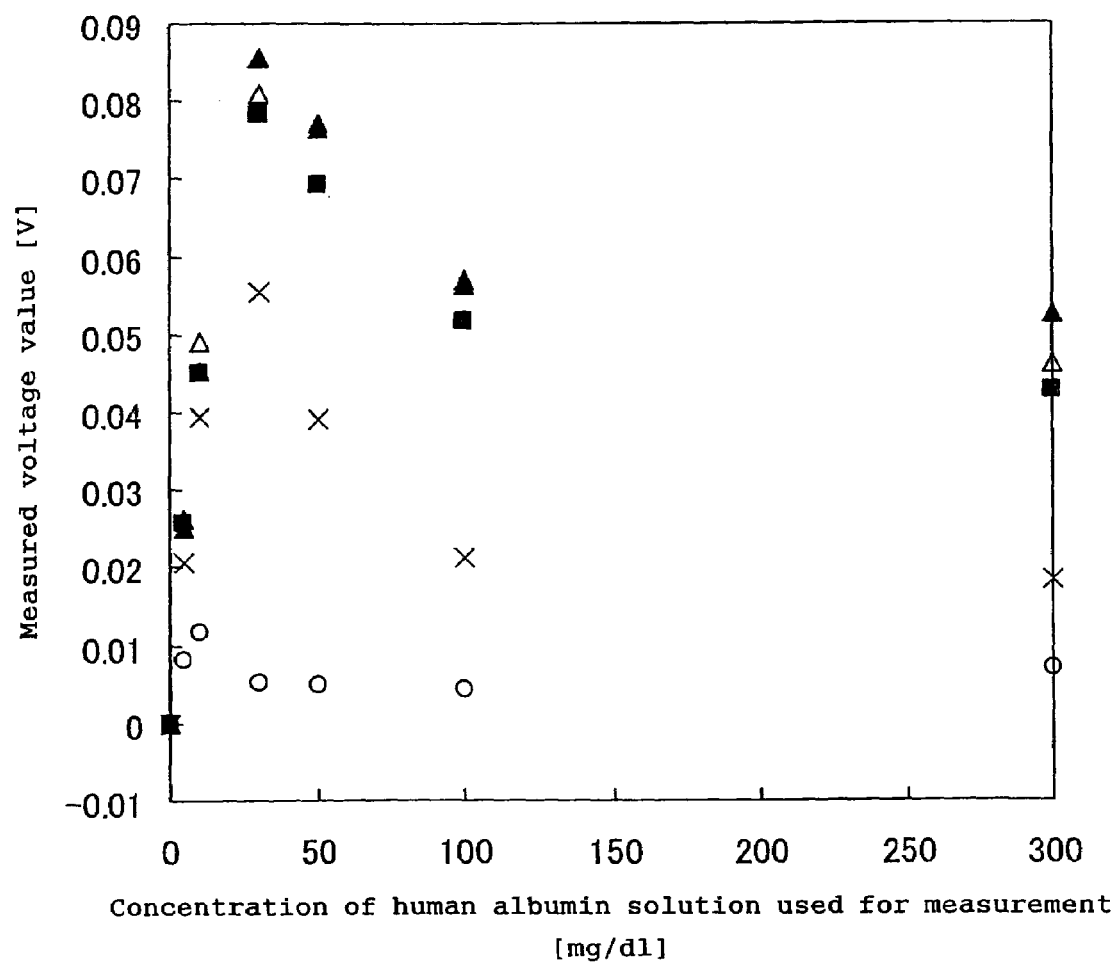
FIG. 11 is a graph representing measurement results of immunoreactions using reagents containing a pimelic acid in Example 5 of the present invention.

FIGS. 4 to 6 show the obtained measurement results. Shown in FIG. 4 were plots representing results about an L(−)-malic acid; shown in FIG. 5 were plots representing results about an L(+)-tartaric acid; shown in FIG. 6 were plots representing results of an itaconic acid. The vertical axis represents a voltage value while the horizontal axis represents the concentration of the human albumin solution used for the measurement.

It was found from FIGS. 4 to 6 that higher measurement values were obtained in using the buffer of pH 4.5 to 5.0 containing an L(−)-malic acid, the buffer of pH 4.0 to 5.0 containing an L(+)-tartaric acid, or the buffer of pH 4.5 to 5.0 containing an itaconic acid, than in using the buffer of the comparative example (X in FIGS. 4 to 6). It was also found that a limitation of a measurement range due to a zone phenomenon that occurred in an antigen excess region was relaxed.

It was found from the above results that, in the immunoreaction measurement method using each buffer containing a dicarboxylic acid having a hydroxyl group, a dicarboxylic acid having a double bond, or the salts of these dicarboxylic acids, a measurement value of an antigen-antibody reaction is improved at least by setting pH of a reaction system to the range of 4.0 to 5.0 in consideration of pH characteristics of those compounds. It was also found that a limitation of a measurement range due to a zone phenomenon that occurs in an antigen excess region is relaxed.

It was further found that, as for the immunoreaction measurement reagent using each buffer containing a dicarboxylic acid having a hydroxyl group, a dicarboxylic acid having a double bond, or the salts of these dicarboxylic acids, the reagent is preferably formulated such that at least pH of a reaction solution becomes 4.0 to 5.0 in consideration of pH characteristics of those compounds.

EXAMPLE 5

In the present example, pH dependencies of effects on an antigen-antibody reaction, exhibited by straight-chain dicarboxylic acids expressed by the chemical formula (1): $HOOC(CH_2)_nCOOH$ (n is an integer), were examined using immunonephelometry. As the straight-chain dicarboxylic acids used were a malonic acid (n=1), a succinic acid (n=2), a glutaric acid (n=3), an adipic acid (n=4), a pimelic acid (n=5), a suberic acid (n=6) and an azelaic acid (n=7).

As the human albumin solution as the sample, the same one as in Example 3 was used. As the antibody solution, the same one as in Example 1 was used.

As the reagent used was one obtained by mixing each below-described buffer containing a malonic acid, a glutaric acid, an adipic acid, a pimelic acid, a suberic acid or an azelaic acid, with the antibody solution including a rabbit antihuman albumin polyclonal antibody, as in Example 1. Also used was one obtained by mixing a below-described buffer containing a succinic acid with the antibody solution including a mouse antihuman albumin monoclonal antibody, as in Example 1.

For examining the pH dependency in the case of using a malonic acid, each buffer of pH 4.0, 4.5, 5.0, 5.5 or 6.0, containing 0.05 M of a malonic acid and 5 wt % of polyethylene glycol 6000, was prepared.

For examining the pH dependency in the case of using a succinic acid, each buffer of pH 4.0, 4.5, 5.0, 5.5 or 6.0, containing 0.05 M of a succinic acid and 5 wt % of polyethylene glycol 6000, was prepared.

For examining the pH dependency in the case of using a glutaric acid, each buffer at pH 4.5, 5.0 or 6.0, containing 0.05 M of a glutaric acid and 5 wt % of polyethylene glycol 6000, was prepared.

For examining the pH dependency in the case of using an adipic acid, each buffer of pH 4.5, 5.0, 5.5 or 6.0, containing 0.05 M of an adipic acid and 5 wt % of polyethylene glycol 6000, was prepared.

For examining the pH dependency in the case of using a pimelic acid, each buffer of pH 4.5, 5.0, 5.5 or 6.0, containing 0.05 M of a pimelic acid and 5 wt % of polyethylene glycol 6000, was prepared.

For examining the pH dependency in the case of using a suberic acid, each buffer of pH 5.0, 5.5 or 6.0, containing 0.05 M of a suberic acid and 5 wt % of polyethylene glycol 6000, was prepared.

For examining the pH dependency in the case of using an azelaic acid, each buffer of pH 5.0, 5.5 or 6.0, containing 0.05 M of an azelaic acid and 5 wt % of polyethylene glycol 6000, was prepared.

Further, in a comparative example, a buffer of pH 7.4, containing 0.05 M of MOPS and 5 wt % of polyethylene glycol 6000, was used; as the antibody solution, the antibody solution including a rabbit antihuman albumin polyclonal antibody was used when comparing with the each solution containing a malonic acid, a glutaric acid, an adipic acid, a pimelic acid, a suberic acid or an azelaic acid; the antibody solution including a mouse antihuman albumin monoclonal antibody was used when comparing with the buffer containing succinic acid. The measurement was performed in the same manner as in Example 3.

Figure 12:
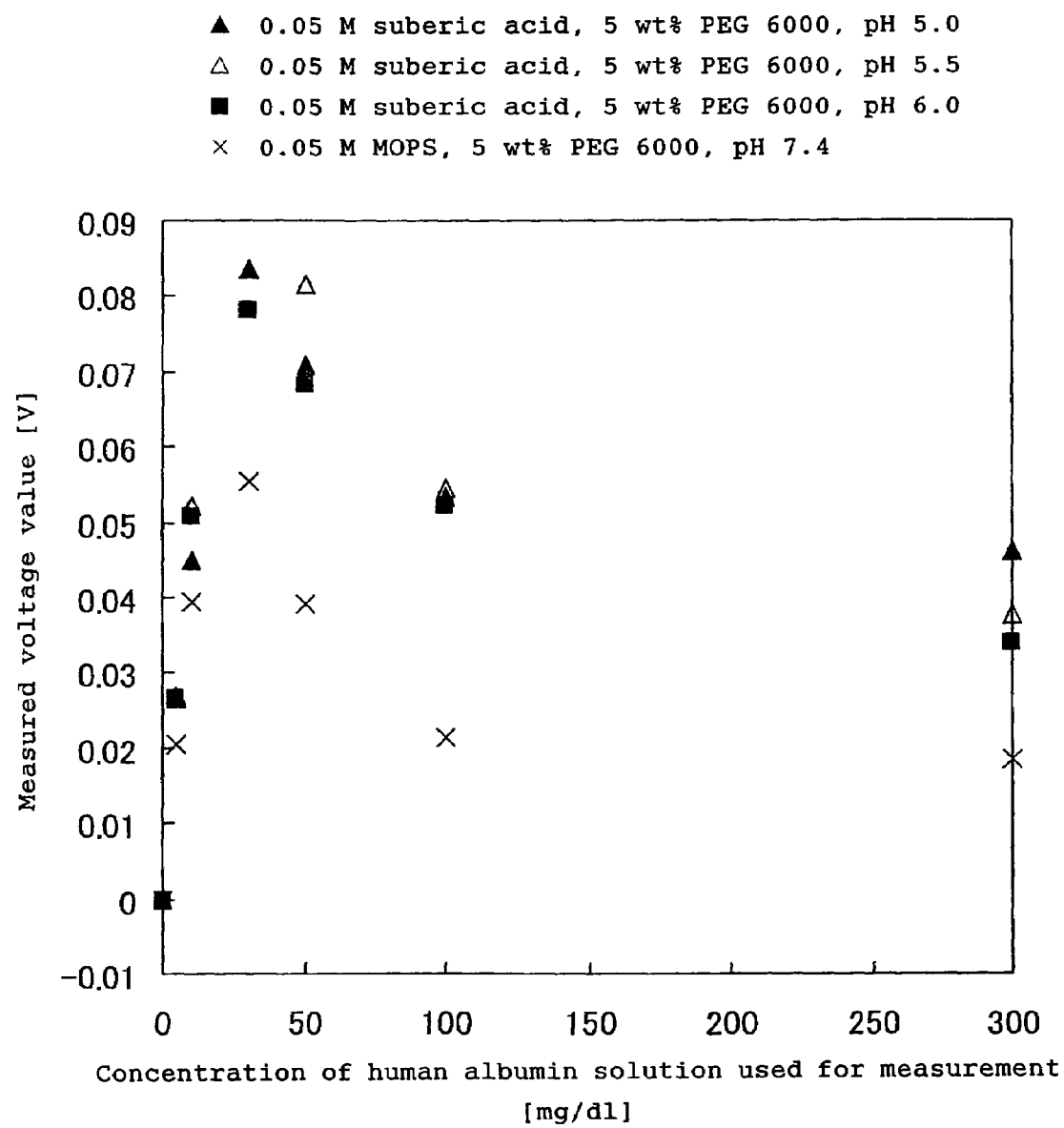
FIG. 12 is a graph representing measurement results of immunoreactions using reagents containing a suberic acid in Example 5 of the present invention.
Figure 13:
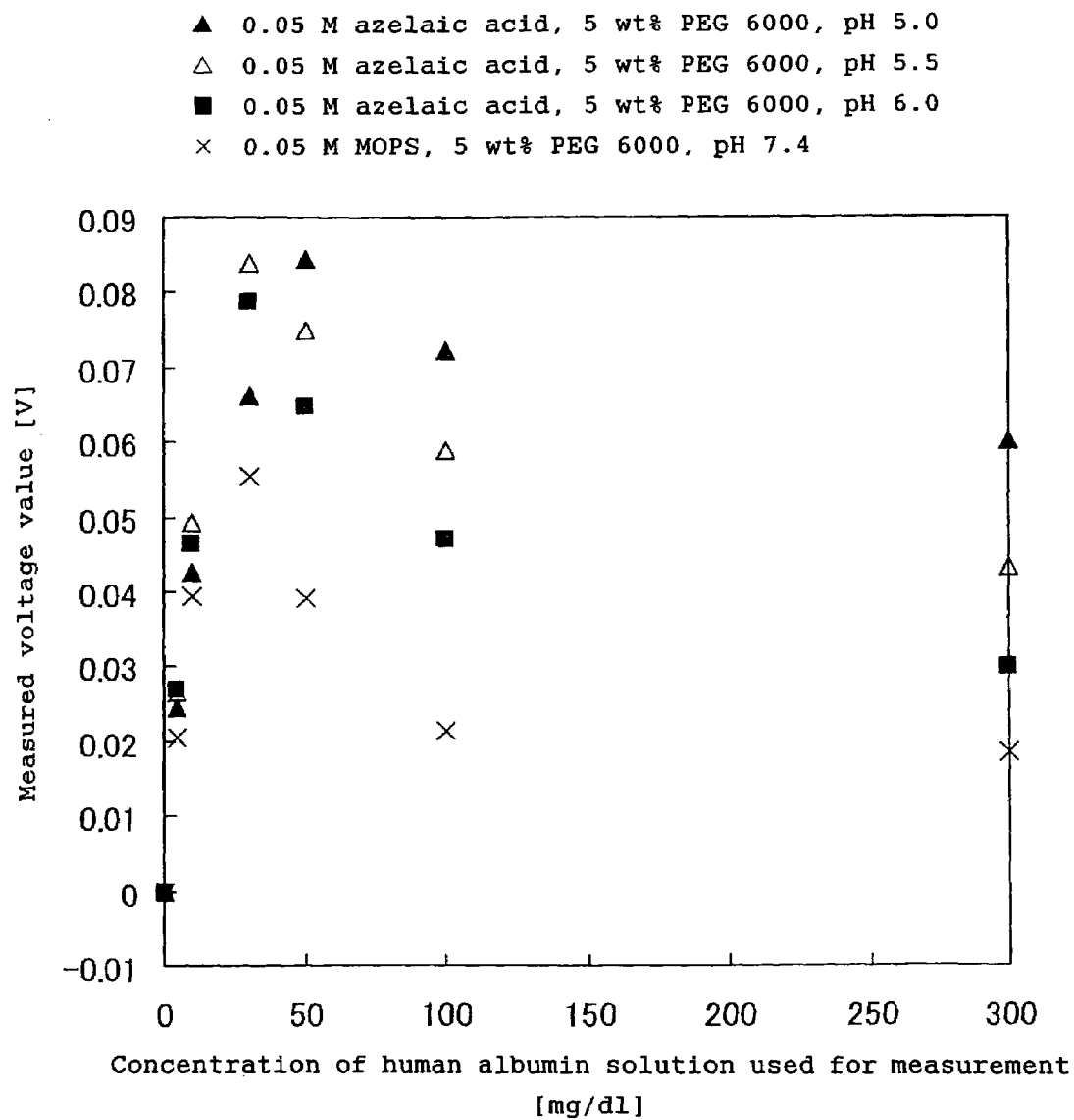
FIG. 13 is a graph representing measurement results of immunoreactions using reagents containing an azelaic acid in Example 5 of the present invention.

FIGS. 7 to 13 show the obtained measurement results. Shown in FIG. 7 were plots representing results about a malonic acid; shown in FIG. 8 were plots representing results about a succinic acid; shown in FIG. 9 were plots representing results about a glutaric acid; shown in FIG. 10 were plots representing results about an adipic acid; shown in FIG. 11 were plots representing results about a pimelic acid; shown in FIG. 12 plots representing results about a suberic acid; shown in FIG. 13 were plots representing results about an azelaic acid. The vertical axis represents a voltage value while the horizontal axis represents the concentration of the human albumin solution used for the measurement.

It was found from FIGS. 7 to 13 that higher measurement values were obtained in using the buffer of pH 4.5 to 6.0 containing a malonic acid, the buffer of pH 5.0 to 6.0 containing a succinic acid, the buffer of pH 5.0 to 6.0 containing a glutaric acid, the buffer of pH 5.0 to 6.0 containing an adipic acid, the buffer of pH 5.0 to 6.0 containing a pimelic acid, the buffer of pH 5.0 to 6.0 containing a suberic acid and the buffer of pH 5.0 to 6.0 containing an azelaic acid, than in using the buffer of the comparative example containing MOPS. It was also found that a limitation of a measurement range due to a zone phenomenon that occurred in an antigen excess region was relaxed.

It was found from the above results that, in the immunoreaction measurement method using each buffer containing a straight-chain dicarboxylic acid expressed by the chemical formula (1): $HOOC(CH_2)_nCOOH$ (n is an integer), or the salt thereof, a measurement value of an antigen-antibody reaction is improved at least by setting pH of a reaction solution to 4.5 to 6.0 in consideration of pH characteristics of those compounds. It was also found that a limitation of a measurement range due to a zone phenomenon that occurs in an antigen excess region is relaxed.

It was further found that, as for the immunoreaction measurement reagent using each buffer containing a straight-chain dicarboxylic acid expressed by the chemical formula (1): $HOOC(CH_2)_nCOOH$ (n is an integer), or the salt thereof, the reagent is preferably formulated such that at least pH of q reaction solution becomes 4.5 to 6.0 when an antigen-antibody reaction occurs, in consideration of pH characteristics of those compounds.

As thus described, it was confirmed from Examples 4 and 5 that, in the immunoreaction measurement method of the present invention, pH of a reaction system can be set to 4.0 to 6.0 by using a compound selected from the group consisting of dicarboxylic acids having a hydroxyl group, dicarboxylic acids having a double bond, straight-chain dicarboxylic acids expressed by the chemical formula (1): $HOOC(CH_2)_nCOOH$ (n is an integer), and the salts of these dicarboxylic acids, while maintaining the effect of improving a measurement value of an antigen-antibody reaction as well as the effect of relaxing a limitation of a measurement range due to a zone phenomenon that occurs in an antigen excess region.

It was also found that as for the immunoreaction measurement reagent of the present invention, the reagent can be formulated such that pH of a reaction system becomes 4.0 to 6.0 when an antigen-antibody reaction occurs, by using at least one compound selected from the group consisting of dicarboxylic acids having a hydroxyl group, dicarboxylic acids having a double bond, straight-chain dicarboxylic acids expressed by the chemical formula (1): $HOOC(CH_2)_nCOOH$ (n is an integer), and the salts of these dicarboxylic acids.

EXAMPLE 6

Next, concentration dependencies of effects on an antigen-antibody reaction, exhibited by at least one compound selected from the group consisting of dicarboxylic acids having a hydroxyl group, dicarboxylic acids having a double bond, straight-chain dicarboxylic acids expressed by the chemical formula (1): $HOOC(CH_2)_nCOOH$ (n is an integer), and the salts of these dicarboxylic acids, were examined.

As for the human albumin solution, the same one as in Example 3 was used. As for the antigen solution, the antibody solution comprising a rabbit antihuman albumin polyclonal antibody, as in Example 1, was used.

As for the buffer used was each buffer prepared in the following method using an L(−)-malic acid, an itaconic acid or a succinic acid.

For examining the concentration dependency in the case of using an L(−)-malic acid, each buffer of pH 5.0, containing 4 wt % of polyethylene glycol 6000 and an L(−)-malic acid at a concentration of 0.01, 0.02, 0.05, 0.1 or 0.2 M, was prepared.

For examining the concentration dependency in the case of using an itaconic acid, each buffer of pH 5.0, containing 4 wt % of polyethylene glycol 6000 and an itaconic acid at a concentration of 0.01, 0.02, 0.05, 0.1 or 0.2 M, was prepared.

For examining the concentration dependency in the case of using a succinic acid, each buffer of pH 5.0, containing 4 wt % of polyethylene glycol 6000 and a succinic acid at a concentration of 0.01, 0.02, 0.05, 0.1 or 0.2 M, was prepared. Further, as a comparative example, a buffer of pH 7.4, containing 0.05 M of MOPS and 4 wt % of polyethylene glycol 6000, was used. As the antibody solution, an antibody solution including a rabbit antihuman albumin polyclonal antibody was used.

The measurement of immunoreaction was performed in the same manner as in Example 3.

Figure 14:
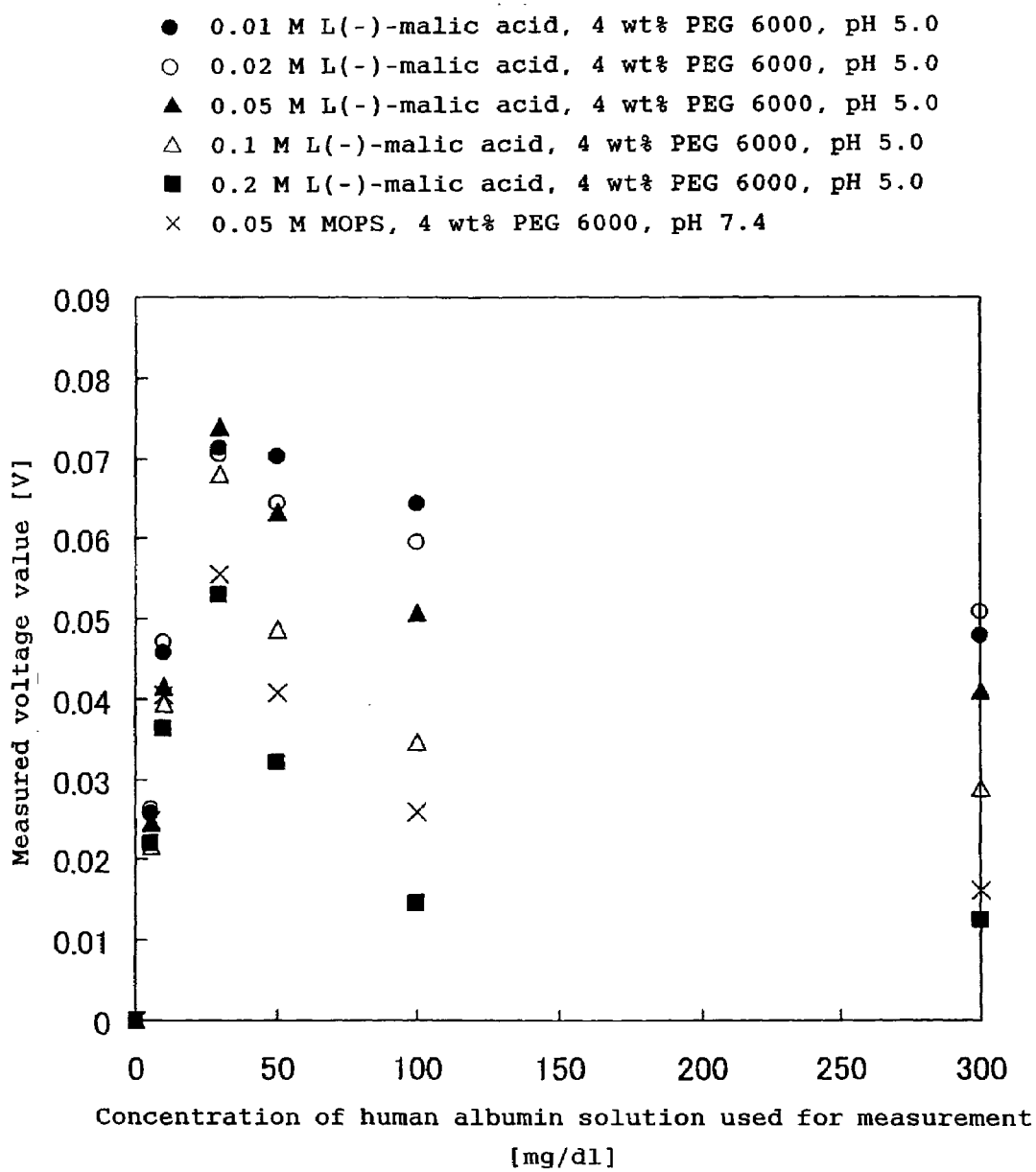
FIG. 14 is a graph representing measurement results of immunoreactions using reagents containing an L(-)-malic acid in Example 6 of the present invention.
Figure 15:
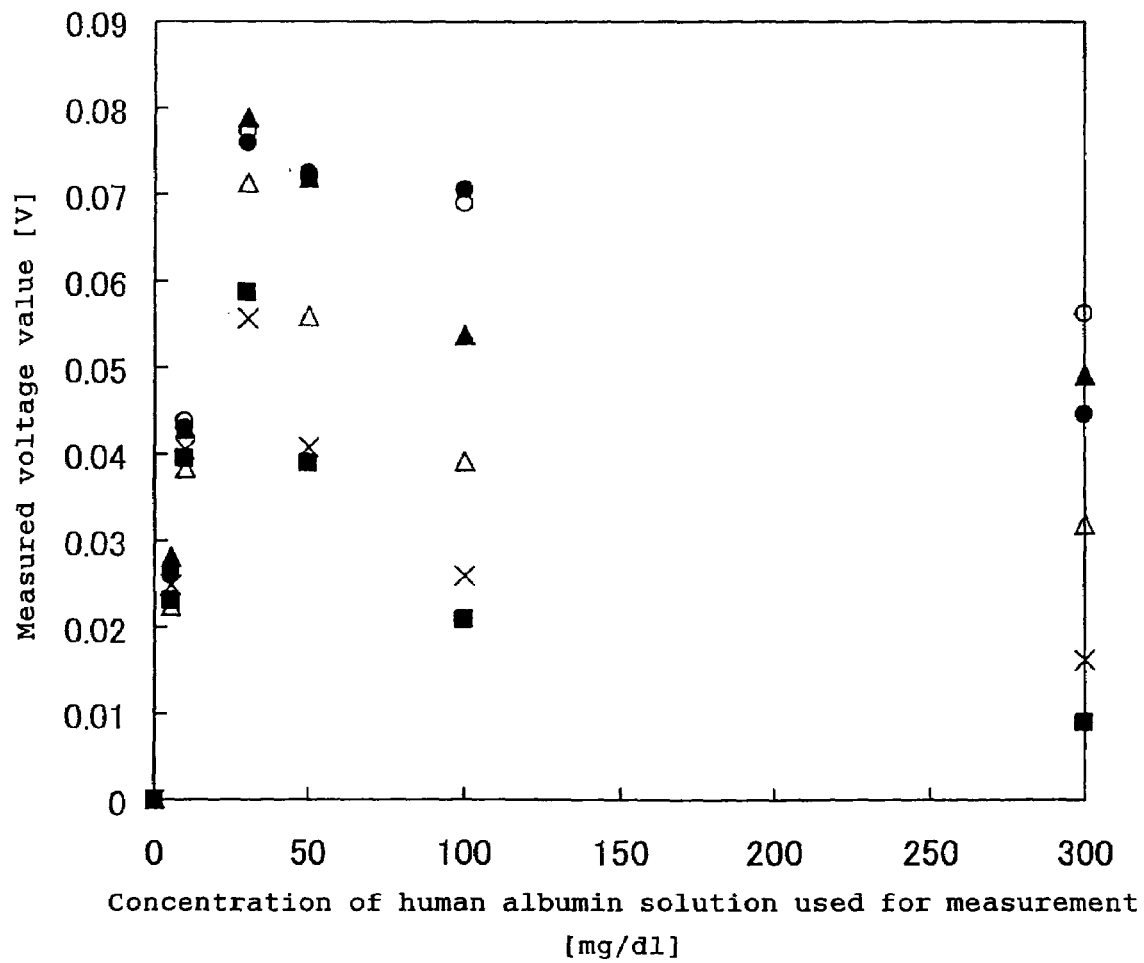
FIG. 15 is a graph representing measurement results of immunoreactions using reagents containing an itaconic acid in Example 6 of the present invention.
Figure 16:
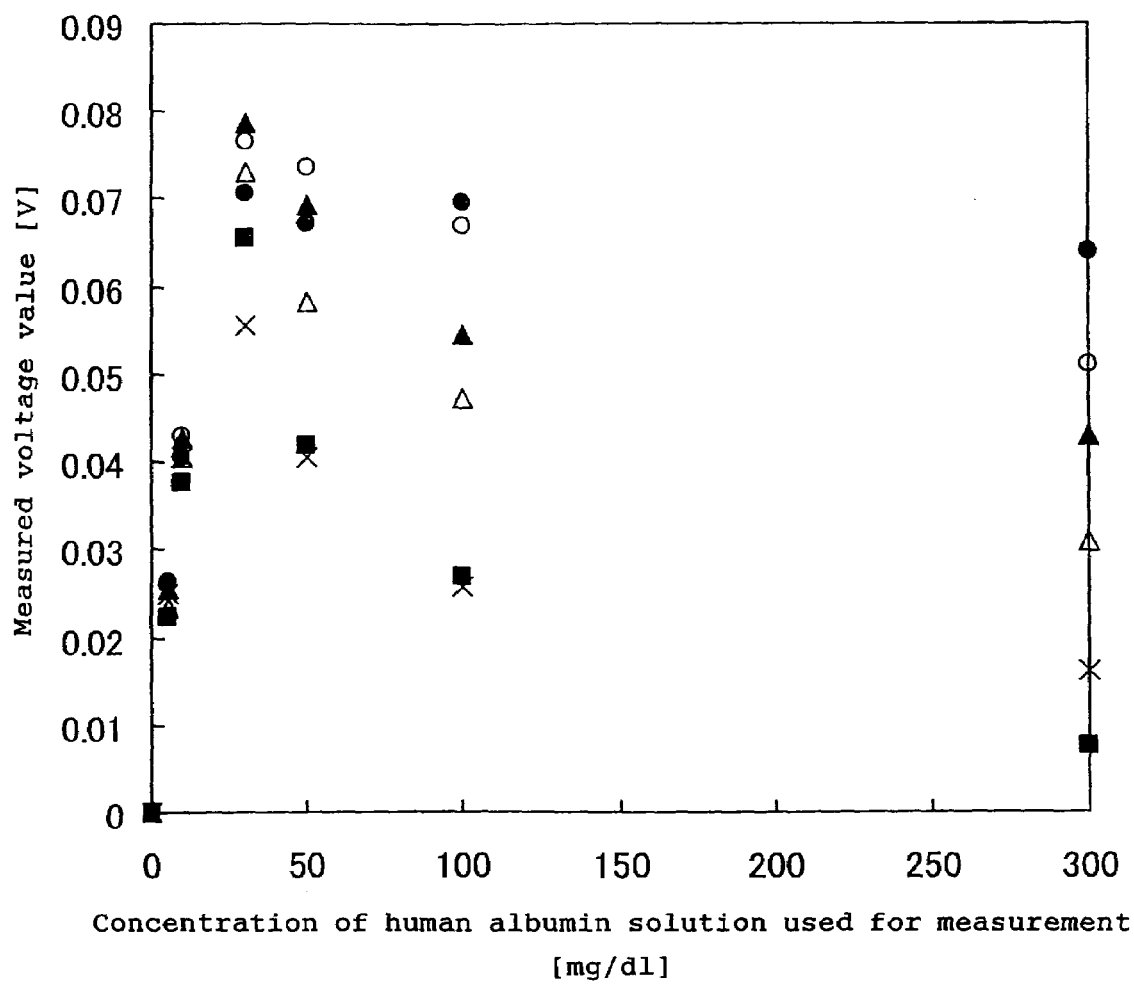
FIG. 16 is a graph representing measurement results of immunoreactions using reagents containing a succinic acid in Example 6 of the present invention.

FIGS. 14 to 16 show the obtained measurement results. Shown in FIG. 14 were plots representing results about an L(−)-malic acid; shown in FIG. 15 were plots representing results about an itaconic acid; shown in FIG. 16 were plots representing results of a succinic acid. The vertical axis represents a voltage value while the horizontal axis represents the concentration of the human albumin solution used for the measurement.

It was found from FIGS. 14 to 16 that, in each case, higher measurement values were shown in using at least one compound selected from the group consisting of dicarboxylic acids having a hydroxyl group, dicarboxylic acids having a double bond, straight-chain dicarboxylic acids expressed by the chemical formula (1): $HOOC(CH_2)_nCOOH$ (n is an integer), and the salts of these dicarboxylic acids, with the concentration range thereof from 0.01 M to 0.1 M, than in using the buffer containing MOPS of the comparative example. It was also found that a limitation of a measurement range due to a zone phenomenon that occurs in an antigen excess region was relaxed.

It was found from the above results that, in the immunoreaction measurement method in accordance with the present invention, the concentration of at least one compound selected from the group consisting of dicarboxylic acids having a hydroxyl group, dicarboxylic acids having a double bond, straight-chain dicarboxylic acids expressed by the chemical formula (1): $HOOC(CH_2)_nCOOH$ (n is an integer), and the salts of these dicarboxylic acids, is preferably set to not higher than 0.1 M. Moreover, when the compound confers a buffering capability to a reaction solution, the concentration is preferably set to 0.01 to 0.1 M.

Similarly to this, it was found that, the immunoreaction measurement reagent in accordance with the present invention is preferably formulated such that the concentration of at least one selected from the group consisting of dicarboxylic acids having a hydroxyl group, dicarboxylic acids having a double bond, straight-chain dicarboxylic acids expressed by the chemical formula (1): $HOOC(CH_2)_nCOOH$ (n is an integer), and the salts of these dicarboxylic acids, is set to not higher than 0.1 M when an antigen-antibody reaction occurs. It was also found that, when the compound provides a reaction solution with a buffering capability, the reagent is preferably formulated such that the concentration becomes 0.01 to 0.1 M.

EXAMPLE 7

Next, an effect on an antigen-antibody reaction in using a mixture of compounds each selected from the group consisting of dicarboxylic acids having a hydroxyl group, dicarboxylic acids having a double bond, straight-chain dicarboxylic acids expressed by the chemical formula (1): $HOOC(CH_2)_nCOOH$ (n is an integer), and the salts of these dicarboxylic acids, was confirmed using immunonephelometry.

As the subject substance, human albumin was used. The human albumin solution was prepared in the same manner as in Example 2, containing human albumin at a concentration of 0, 5, 10, 20, 30, 50, 70, 100, 200, or 300 mg/dl. As for the antibody solution, the antibody solution including a rabbit antihuman albumin polyclonal antibody, as in Example 1, was used.

As for the buffer used was one containing, together with a succinic acid, an L(−)-malic acid, an L(+)-tartaric acid, an itaconic acid, a fumaric acid or a maleic acid, with the pH thereof set to 4.5. At pH 4.5, a succinic acid has no effect, and thereby each effect of an L(−)-malic acid, an L(+)-tartaric acid, an itaconic acid, a fumaric acid or a maleic acid is easy to confirm. As a comparative example, a buffer containing only a succinic acid was used. Table 1 shows a composition and pH of each buffer.

TABLE 1

| | Composition | pH |
|---|---|---|
| 1 | 0.02 M of L(−)-malic acid, 0.1 M of succinic acid, 4 wt % of polyethylene glycol 6000 | 4.5 |
| 2 | 0.02 M of L(+)-tartaric acid, 0.1 M of succinic acid, 4 wt % of polyethylene glycol 6000 | 4.5 |
| 3 | 0.02 M of itaconic acid, 0.1 M of succinic acid, 4 wt % of polyethylene glycol 6000 | 4.5 |
| 4 | 0.02 M of fumaric acid, 0.1 M of succinic acid, 4 wt % of polyethylene glycol 6000 | 4.5 |
| 5 | 0.02 M of maleic acid, 0.1 M of succinic acid, 4 wt % of polyethylene glycol 6000 | 4.5 |
| Comp. | 0.12 M of succinic acid, 4 wt % of polyethylene glycol 6000 | 4.5 |

For the measurement, a fluorescence spectrophotometer (manufactured by Shimadzu Corporation, model number: RF-5300PC) was used. A constant-temperature cell holder (manufactured by Shimadzu Corporation, model number: 206-15440) was placed in a sample chamber of the spectrofluorometer, and then connected to a constant-temperature bath (manufactured by Taitec Corporation, trade name: COOLNIT BATH EL-15). Water maintained at 25° C. was circulated so as to maintain a constant temperature in measurement. Conditions for the measurement using the spectrofluorometer were: excitation light and fluorescent light each had a wavelength of 670 nm, band width was 3 nm both at the fluorescence side and the excitation side, and sensitivity was set to be high.

The measurement was performed as follows. 2.87 ml of the buffer and 0.1 ml of the antibody solution were mixed together while stirring, and to this mixture, 0.03 ml of the human albumin solution was added, followed by mixing while stirring, to obtain a reaction solution. That is, in the reaction solution, the final concentration of the antibody was about 0.10 mg/ml and the final concentration of human albumin was equivalent to one obtained by multiplying the concentration of the human albumin solution used in measurement by 0.01. The mixture was transferred to a quartz cell for fluorescence analysis, while the quartz cell was placed in the spectrofluorometer, and a T-type thermocouple (obtained from RS Components K. K., model number: 219-4696) was immersed in the cell. Time-course measurement was started 2 minutes after the addition of human albumin, and was continued every 0.04 seconds for 300 seconds.

A temperature in the cell during measurement was monitored with a digital multithermometer (manufactured by Advantest, model number: TR2114) connected to the T-type thermocouple. Any influence of contamination of the cell on the measurement was removed by compensating measurement values based on measurement which had been conducted with pure water placed in the cell before measuring each reaction. The respective measurement values obtained in measurement over 200 to 300 seconds were averaged, and the resultant average value was regarded as a measurement value for the human albumin solution having each concentration. After the measurement, in order to observe the influence of mixing of each buffer, the antibody solution, and the human albumin solution having each concentration on the pH of the reaction solution, the pH of the mixed solution was measured using a pH meter.

As a result, any pH of the mixed solution including each buffer, the antibody solution, and the human albumin solution at each concentration in each measurement was the same as the pH of the buffer. The temperature in the cell during measurement, which was measured with the thermocouple, was kept at 25.5±1° C.

Figure 17:
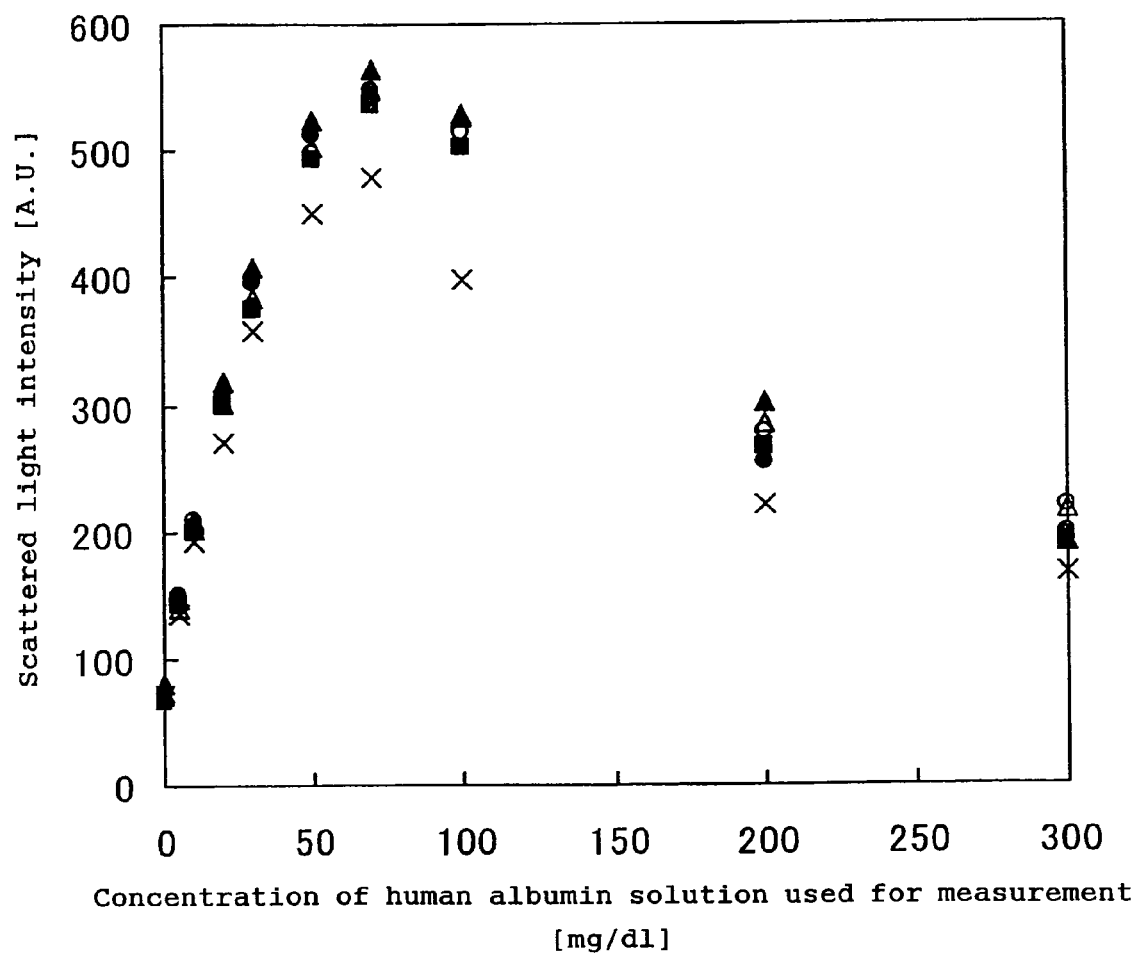
FIG. 17 is a graph representing measurement results of immunoreactions in Example 7 of the present invention.

FIG. 17 shows the measurement results. Shown in FIG. 17 were plots representing results of measurement of the human albumin solution having each concentration up to 300 mg/dl with respect to each buffer. The vertical axis represents scattered light intensity while the horizontal axis represents the concentration of the human albumin solution used for the measurement.

Measurement values were improved more in using each buffer containing an L(−)-malic acid, an L(+)-a tartaric acid, an itaconic acid, a fumaric acid or a maleic acid, rather than in using the buffer containing only a succinic acid. Further, a limitation of a measurement range due to a zone phenomenon that occurred in an antigen excess region was relaxed.

It was confirmed from the above results that, even when compounds are used in mixture, the compounds each selected from the group consisting of dicarboxylic acids having a hydroxyl group, dicarboxylic acids having a double bond, straight-chain dicarboxylic acids expressed by the chemical formula (1): $HOOC(CH_2)_nCOOH$ (n is an integer), and the salts of these dicarboxylic acids, the similar effect on an antigen-antibody reaction was exhibited to the effect in the case of using a single compound selected from the same.

EXAMPLE 8

Next, regarding a pH range showing an effect on an antigen-antibody reaction when compounds each selected from the group consisting of dicarboxylic acids having a hydroxyl group, dicarboxylic acids having a double bond, straight-chain dicarboxylic acids expressed by the chemical formula (1): $HOOC(CH_2)_nCOOH$ (n is an integer), and the salts of these dicarboxylic acids, were used in mixture, whether or not the effect is increased by a synergistic action was studied using immunonephelometry.

As the subject substance, human albumin was used. As the human albumin solution, the same one as in Example 3 was used. As for the antibody solution, the antibody solution comprising a rabbit antihuman albumin polyclonal antibody, as in Example 1, was used.

As the buffer, each buffer of pH 4.0, 4.5, 5.0, 5.5 or 6.0, containing 0.025 M of an L(+)-tartaric acid, 0.025 M of a succinic acid and 4 wt % of polyethylene glycol 6000, was used. When an L(+)-tartaric acid and a succinic acid were singly used, the effective pH of an L(+)-tartaric acid and a succinic acid were 4.0 to 5.0 and 5.0 to 6.0, respectively.

As a comparative example, a buffer of pH 7.4, containing 0.05 M of MOPS and 4 wt % of polyethylene glycol 6000, was used, and as the antibody solution, the same antibody solution including a rabbit antihuman albumin polyclonal antibody as described above was used.

Immunoreactions were measured in the same manner as in Example 3.

FIG. 18 shows the obtained measurement results. The vertical axis represents a voltage value while the horizontal axis represents the concentration of the human albumin solution used for the measurement.

When the buffer containing an L(+)-tartaric acid and a succinic acid was used, the effective pH respective to an antigen-antibody reaction was 4.5 to 6.0, indicating that the range of the effective pH was enlarged from the range of the effective pH in using the buffer singly containing an L(+)-tartaric acid or a succinic acid.

It was confirmed from the above that combination of characteristics of compounds each selected from the group consisting of dicarboxylic acids having a hydroxyl group, dicarboxylic acids having a double bond, straight-chain dicarboxylic acids expressed by the chemical formula (1): $HOOC(CH_2)_nCOOH$ (n is an integer), and the salts of these dicarboxylic acids, allows enlargement of an effective pH range.

INDUSTRIAL APPLICABILITY

As described above, according to the present invention, an immunoreaction measurement method and immunoreaction measurement reagent for use in the method, capable of easily improving a measurement value, can be provided. Moreover, an immunoreaction measurement reagent and an immunoreaction measurement reagent for use in the method, capable of relaxing a limitation of a measurement range due to a zone phenomenon that occurs in an antigen excess region, can be provided.

The invention claimed is:

1. An immunoreaction measurement method for measuring an antigen or antibody contained as a subject substance in a sample, comprising the steps of:
    (A) mixing said sample; at least one compound selected from the group consisting of tartaric acid, itaconic acid, straight-chain dicarboxylic acids expressed by the chemical formula (1): $HOOC(CH_2)_nCOOH$ (n is an integer from 1 to 7), and the salts of these dicarboxylic acids; and an antibody or antigen as a specifically binding substance capable of specifically binding to said subject substance, to obtain an acidic reaction solution; and (B) detecting in said reaction solution an antigen-antibody complex generated by an antigen-antibody reaction of said subject substance and said specifically binding substance, wherein the pH of said reaction solution is set to 5.0 to 6.0 when said compound comprises at least one selected from the group consisting of said straight-chain dicarboxylic acids and salts of these dicarboxylic acids, and the pH of said reaction solution is set to 4.5 to 5.0 when said compound comprises at least one selected from the group consisting of said tartaric acid, said itaconic acid and salts of these dicarboxylic acids.

2. The immunoreaction measurement method in accordance with claim 1, wherein said reaction solution is further mixed with a buffer in said step (A).

3. The immunoreaction measurement method in accordance with claim 1, wherein, in said reaction solution, the concentration of said at least one compound selected from the group consisting of tartaric acid, itaconic acid straight-chain dicarboxylic acids expressed by the chemical formula (1): $HOOC(CH_2)_n COOH$ (n is an integer from 1 to 7), and the salts of these dicarboxylic acids, is set to not higher than 0.1 M.

4. The immunoreaction measurement method in accordance with claim 1, wherein, in said reaction solution, the concentration of said at least one compound selected from the group consisting of tartaric acid, itaconic acid, straight-chain dicarboxylic acids expressed by the chemical formula (1): $HOOC(CH_2)_n COOH$ (n is an integer from 1 to 7), and the salts of these dicarboxylic acids, is set to the range of 0.01 M to 0.1 M.

5. The immunoreaction measurement method in accordance with claim 1, wherein, in said reaction solution, the concentration of said at least one compound selected from the group consisting of tartaric acid, itaconic acid, straight-chain dicarboxylic acids expressed by the chemical formula (1): $HOOC(CH_2)_n COOH$ (n is an integer from 1 to 7), and the salts of these dicarboxylic acids, is set to the range of 0.01 M to 0.05 M.

6. The immunoreaction measurement method in accordance with claim 1, wherein said reaction solution contains polyethylene glycol in an amount of not smaller than 2 wt % and not larger than 6 wt %.

7. The immunoreaction measurement method in accordance with claim 1, wherein said antigen-antibody complex is an agglutination complex.

8. The immunoreaction measurement method in accordance with claim 7, wherein said agglutination complex is detected by measuring optical variations attributed to said agglutination complex.

9. The immunoreaction measurement method in accordance with claim 8, wherein said optical variations are variations in intensity of scattered light.

10. The immunoreaction measurement method in accordance with claim 1, wherein said specifically binding substance is an antibody comprising a monoclonal antibody.

11. The immunoreaction measurement method in accordance with claim 1, wherein said specifically binding substance includes at least two sort or more of monoclonal antibodies.

12. The immunoreaction measurement method in accordance with claim 1, wherein said antigen is human albumin.

* * * * *